United States Patent
Kashkarov et al.

(10) Patent No.: US 8,092,484 B2
(45) Date of Patent: Jan. 10, 2012

(54) EMBOLUS BLOOD CLOT FILTER WITH POST DELIVERY ACTUATION

(75) Inventors: Alexander Germanovich Kashkarov, St. Petersburg (RU); Andrzej J. Chanduszko, Chandler, AZ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/096,856

(22) PCT Filed: Dec. 29, 2006

(86) PCT No.: PCT/US2006/062719
§ 371 (c)(1),
(2), (4) Date: Aug. 13, 2009

(87) PCT Pub. No.: WO2007/079407
PCT Pub. Date: Jul. 12, 2007

(65) Prior Publication Data
US 2009/0306703 A1    Dec. 10, 2009

Related U.S. Application Data

(60) Provisional application No. 60/754,633, filed on Dec. 30, 2005.

(51) Int. Cl.
*A61M 29/00* (2006.01)
(52) U.S. Cl. .................................................. 606/200
(58) Field of Classification Search .................. 606/108, 606/157, 158, 200; 623/1.11, 1.23
See application file for complete search history.

(56) References Cited

U.S. PATENT DOCUMENTS

| | | |
|---|---|---|
| 4,425,908 A | 1/1984 | Simon |
| 4,494,531 A | 1/1985 | Gianturco |
| 4,688,553 A | 8/1987 | Metals |
| 4,817,600 A * | 4/1989 | Herms et al. .................. 606/200 |
| 5,108,418 A | 4/1992 | Lefebvre |
| 5,669,933 A | 9/1997 | Simon et al. |
| 5,709,704 A | 1/1998 | Nott et al. |
| 5,776,162 A | 7/1998 | Kleshinski |

(Continued)

FOREIGN PATENT DOCUMENTS

EP          188927 B1         7/1989

(Continued)

OTHER PUBLICATIONS

International Search Report, PCT/US2006/062719.

(Continued)

*Primary Examiner* — Elizabeth Houston
*Assistant Examiner* — Sarah Webb
(74) *Attorney, Agent, or Firm* — Garvey, Smith, Nehrbass & North, L.L.C.; Seth M. Nehrbass; Charles C. Garvey, Jr.

(57) ABSTRACT

A removable blood clot filter includes a number of locator members and anchor members, and a bio-resorbable structure that causes locator members and/or anchor members to deploy to an initial configuration which changes when the bio-resorbable structure is resorbed. The bio-resorbable structure causes the filter locator members and/or anchor members to press against the vessel wall sufficient to locate and anchor the filter upo delivery. After the bio-resorbable structure is resorbed, the locator members and/or anchor members change shape to apply less pressure against the vessel wall. The bio-resorbable structure may be activated by exposure to radiation so that actuation of the locator members and/or anchor members can be enabled or initiated by a clinician.

18 Claims, 17 Drawing Sheets

U.S. PATENT DOCUMENTS

| | | | |
|---|---|---|---|
| 5,800,457 A | 9/1998 | Gelbfish | |
| 5,836,968 A | 11/1998 | Simon et al. | |
| 6,007,558 A * | 12/1999 | Ravenscroft et al. | 606/200 |
| 6,080,178 A | 6/2000 | Meglin | |
| 6,156,055 A | 12/2000 | Ravenscroft | |
| 6,176,871 B1 | 1/2001 | Pathak et al. | |
| 6,193,739 B1 | 2/2001 | Chevillon et al. | |
| 6,258,026 B1 | 7/2001 | Ravenscroft et al. | |
| 6,267,776 B1 | 7/2001 | O'Connell | |
| 6,273,900 B1 | 8/2001 | Nott et al. | |
| 6,331,183 B1 | 12/2001 | Suon | |
| 6,350,277 B1 * | 2/2002 | Kocur | 623/1.11 |
| 6,436,120 B1 | 8/2002 | Meglin | |
| 6,443,972 B1 | 9/2002 | Bosma et al. | |
| 6,468,290 B1 | 10/2002 | Weldon et al. | |
| 6,517,559 B1 * | 2/2003 | O'Connell | 606/200 |
| 6,540,767 B1 | 4/2003 | Walak et al. | |
| 6,589,266 B2 * | 7/2003 | Whitcher et al. | 606/200 |
| 6,623,506 B2 | 9/2003 | McGuckin, Jr. et al. | |
| 6,872,217 B2 | 3/2005 | Walak et al. | |
| 7,056,286 B2 | 6/2006 | Ravenscroft et al. | |
| 7,699,867 B2 * | 4/2010 | Hendriksen et al. | 606/200 |
| 2001/0003796 A1 | 6/2001 | Yang et al. | |
| 2001/0039432 A1 | 11/2001 | Whitcher et al. | |
| 2003/0071285 A1 | 4/2003 | Tsukernik | |
| 2003/0074019 A1 | 4/2003 | Gray et al. | |
| 2003/0187495 A1 | 10/2003 | Cully et al. | |
| 2004/0073252 A1 | 4/2004 | Goldberg et al. | |
| 2004/0186512 A1 | 9/2004 | Bruckheimer et al. | |
| 2004/0193209 A1 | 9/2004 | Pavcnik et al. | |
| 2005/0055045 A1 | 3/2005 | DeVries et al. | |
| 2005/0085847 A1 | 4/2005 | Galdonik et al. | |
| 2005/0159771 A1 | 7/2005 | Petersen | |
| 2005/0159773 A1 | 7/2005 | Broome et al. | |
| 2005/0163821 A1 | 7/2005 | Sung et al. | |
| 2005/0177224 A1 | 8/2005 | Fogarty et al. | |
| 2005/0234503 A1 | 10/2005 | Ravenscroft et al. | |
| 2005/0277977 A1 | 12/2005 | Thornton | |
| 2006/0025852 A1 * | 2/2006 | Armstrong et al. | 623/1.17 |
| 2006/0036279 A1 | 2/2006 | Eidenschink et al. | |
| 2006/0095068 A1 | 5/2006 | WasDyke et al. | |

FOREIGN PATENT DOCUMENTS

| | | |
|---|---|---|
| WO | WO 2006/124405 A2 | 11/2006 |
| WO | WO 2007/021340 A1 | 2/2007 |

OTHER PUBLICATIONS

International Preliminary Report on Patentability and Written Opinion of the International Searching Authority in PCT/US06/62719.

* cited by examiner

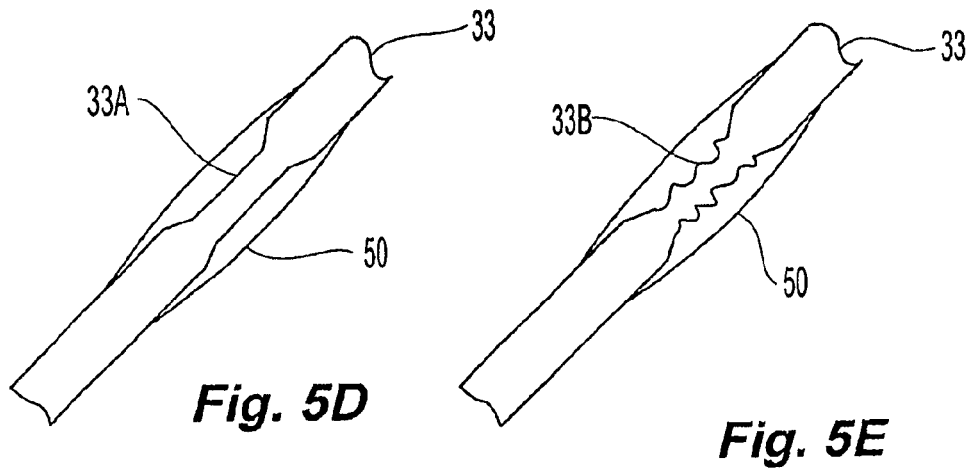
Fig. 5D
Fig. 5E
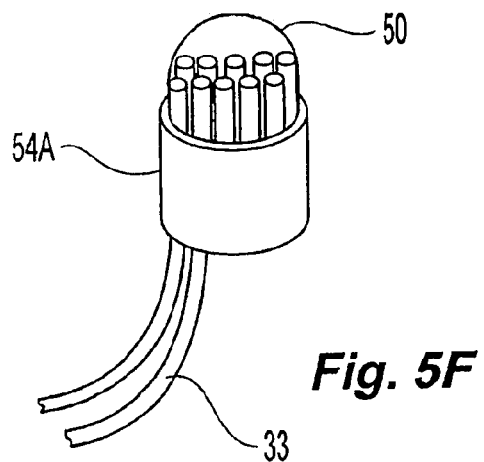
Fig. 5F

EMBOLUS BLOOD CLOT FILTER WITH POST DELIVERY ACTUATION

This is a National Stage application under 35 U.S.C. 371 of International Application No. PCT/US2006/062719, filed Dec. 29, 2006, which claims the benefit of priority to U.S. Provisional Patent Application No. 60/754,633, filed Dec. 30, 2005 each of which is incorporated by reference in its entirety. This invention is related to the subject matter shown and described in the following: (i) PCT International Application No. PCT/US06/62722, filed Dec. 29, 2006, entitled "Removable Blood Clot Filter with Edge For Cutting Through the Endothelium" and claiming the benefit of priority to U.S. Provisional Patent Application No. 60/754,600, filed Dec. 30, 2005; (ii) PCT International Application No. PCT/US06/62733, filed Dec. 29, 2006, entitled "Embolus Blood Clot Filter Removal System and Method," and claiming the benefit of priority to U.S. Provisional Patent Application No. 60/754,598, filed Dec. 30, 2005; (iii) PCT International Application No. PCT/US06/62725, filed Dec. 29, 2006, entitled "Embolus Blood Clot Filter Delivery System," and claiming the benefit of priority to U.S. Provisional Patent Application No. 60/754,636, filed Dec. 30, 2005; (iv) PCT International Application No. PCT/US06/62720, filed Dec. 29, 2006, entitled "Embolus Blood Clot Filter with Floating Filter Basket," and claiming the benefit of priority to U.S. Provisional Patent Application No. 60/754,599, filed Dec. 30, 2005; and (v) PCT International Application No. PCT/US06/62730, filed Dec. 29, 2006, entitled "Embolus Blood Clot Filter with Bio-Resorbable Coated Filter Members," and claiming the benefit of priority to U.S. Provisional Patent Application No. 60/754,597, entitled "Embolus Blood Clot Filter with Retainers on Locator Filter Members," filed Dec. 30, 2005, each of which is hereby incorporated by reference in its entirety.

TECHNICAL FIELD

This invention relates to a filter device that can be placed in a blood vessel to reduce the risk of embolisms and, more particularly to a blood clot filter including post-delivery actuation capability to reduce the potential for damage to the blood vessel.

BACKGROUND ART

In recent years, a number of medical devices have been designed which are adapted for compression into a small size to facilitate introduction into a vascular passageway and which are subsequently expandable into contact with the walls of the passageway. These devices include, among others, blood clot filters which expand and are held in position by engagement with the inner wall of a vein, such as the vena cava. Vena cava filters are known in the art as described, for example, in U.S. Pat. Nos. 4,425,908, 5,669,933 and 5,836,968 and European Patent Office publication 0 188 927 A2, which are hereby incorporated by reference in their entirety. Such filters may include structure to anchor the filter in place within the vena cava, such as elongate diverging anchor members with hooked ends that penetrate the vessel wall and positively prevent longitudinal migration in either direction within the vessel. Such filters also may include structure to locate the filter within the blood vessel, such as near or along the centerline of the vessel. Such structure may consist of a number of locator members which press against the walls of the vessel with approximately equal force, thus causing the center of the filter to move to the centerline of the vessel. A filter including anchor members having hooked ends and locator members is disclosed in U.S. Pat. No. 6,258,026, which is hereby incorporated by reference in its entirety. Once the filter is positioned along the centerline, the anchor members can hook into the vessel wall in locations which help to hold the filter along the vessel centerline. Within a few weeks the endothelium layer grows over the anchors and locator members where they contact the wall, further holding the filter in place.

Blood filters which use anchor members as described above suffer from the disadvantage that the lateral force applied by anchor members to press hooks into the wall of the blood vessel continues to be applied even after the filter has been centered and anchored in place by the hooks and endothelium overgrowth. The continued application of force against the vessel wall by anchor members can lead to vessel damage or injury. Accordingly, there is a need for a blood filter that can secure itself in the vessel and reduce or otherwise remove the force applied to the vessel's walls after the filter is anchored in position.

DISCLOSURE OF INVENTION

The various embodiments provide a blood filter that changes shape or repositions filter members after installation in a blood vessel. The blood filter may include locator members and anchor members. A bio-resorbable retainer retains locator members in a first configuration after installation in a blood vessel until the retainer is resorbed. After the retainer is resorbed, the locator members change shape to a second configuration. The locator members may be configured, so that when the bio-resorbable retainer retains a portion of the members, the ends of the locators are extended radially. When the filter is inserted in the blood vessel with the locators so extended in the first configuration, the locator members apply pressure against the walls of the blood vessel, which acts to position the filter near the centerline of the blood vessel. After the filter has been in the blood vessel for a period of time, the bio-resorbable retainer is resorbed allowing the locator members to reposition into a second configuration, thereby reducing the force applied to the walls of the blood vessel.

In yet another embodiment, a filter to be placed in a flow of blood through a vessel includes anchor members with a bio-resorbable structure which is configured to cause the anchor members to extend radially outward in a first configuration so that when inserted in the blood vessel, the anchor members apply sufficient force against the vessel walls to cause hooks on the ends of the anchors to enter and implant in the walls. After the filter has been in the blood vessel for a period of time, the displacement material is resorbed, thereby removing the radial displacement of the anchors in a second configuration, and thus reducing the force applied against the vessel walls, leaving the hooks implanted in the walls.

In yet a further aspect of the present invention, a filter is provided to be placed in a flow of blood through a vessel in which the locator members include a hook on their distal ends. In order to permit the locator members to reposition from a first configuration to a second configuration, the hooks are covered or encompassed in a bio-resorbable material. The covered hooks are able to slide along the endothelial layer of the blood vessel as the members reconfigure. After the filter has been positioned in the blood vessel for a period of time, the bio-resorbable material covering the hook is resorbed, uncovering the hooks so that the locator member hooks can engage the vessel walls, thereby helping to hold the filter in position within the vessel.

In yet an additional aspect of the various embodiments, a filter is provided to be placed in a flow of blood through a vessel in which one or more of the above described features are included in the same filter.

Another embodiment provides a method of centering a blood filtering device within a blood vessel in which a bio-resorbable material facilitates positioning of the filter and/or results in a change of shape of filter members after the filter has been implanted in order to reduce the force applied against vessel walls by the filter members.

BRIEF DESCRIPTION OF THE DRAWINGS

The accompanying drawings, which are incorporated herein and constitute part of this specification, illustrate exemplary embodiments of the invention, and, together with the general description given above and the detailed description given below, explain features of the invention.

FIG. 5D illustrates a living hinge formed by a smaller constant cross section of an elongate filter member covered with bio-resorbable material.

FIG. 5E illustrates another form of hinge using a changing cross section hinge for an elongate filter member covered with bio-resorbable material.

FIG. 5F illustrates an alternative technique of controlling deployment force with the use of a non-resorbable sleeve and bio-resorbable material.

MODE(S) FOR CARRYING OUT THE INVENTION

The various embodiments will be described in detail with reference to the accompanying drawings. Wherever possible, the same reference numbers will be used throughout the drawings to refer to the same or like parts.

As used herein, the terms "about" or "approximately" for any numerical values or ranges indicates a suitable dimensional tolerance that allows the part or collection of components to function for its intended purpose as described herein. Also, as used herein, the terms "patient," "host" and "subject" refer to any human or animal subject and are not intended to limit the systems or methods to human use, although use of the subject invention in a human patient represents a preferred embodiment.

Figure 1:
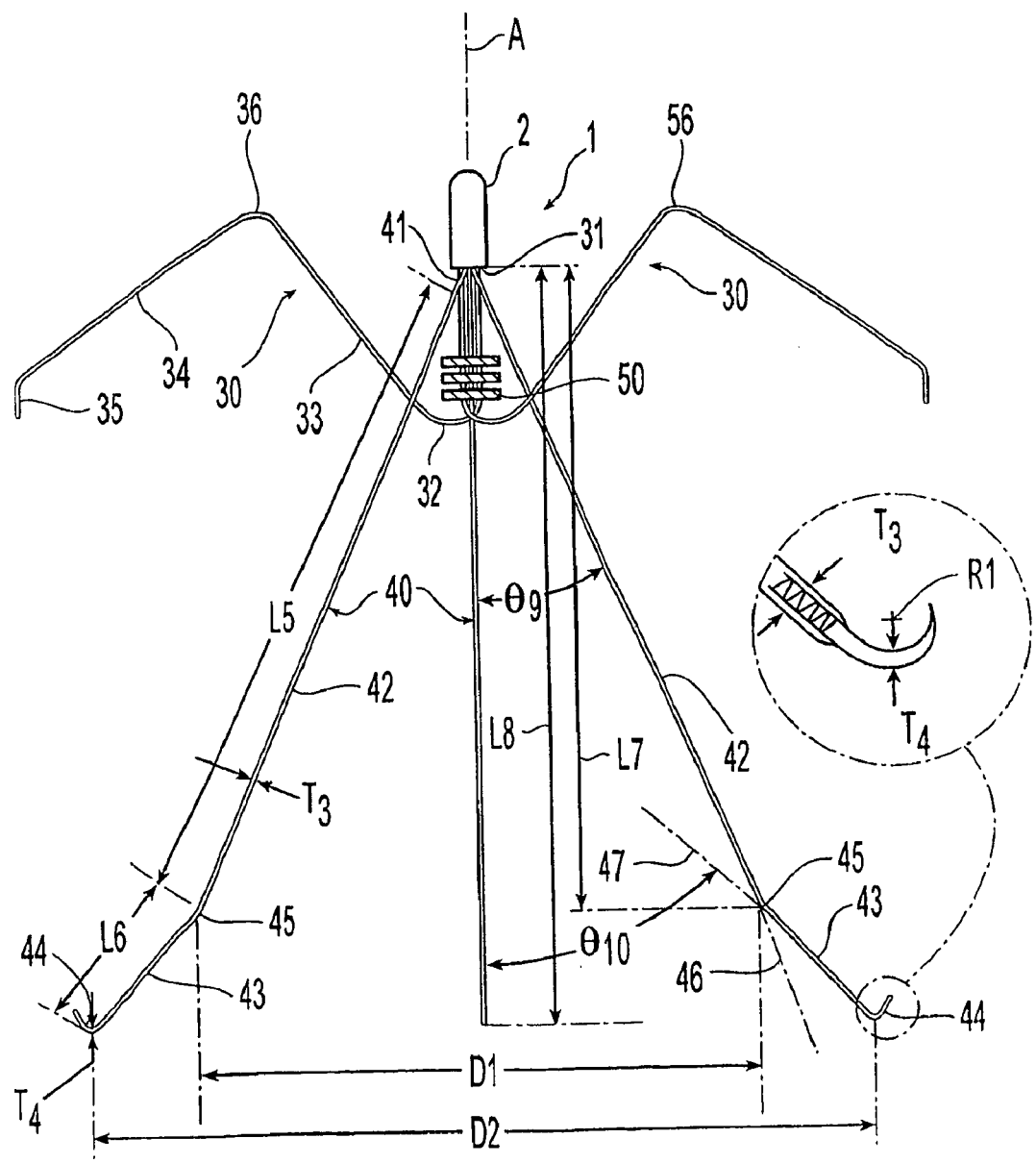
FIG. 1 is a perspective view of an embodiment of the blood filter.

A blood filter is a device suitable for placement in a flow of blood flow through a blood vessel, such as the vena cava, to filter out blood clots. As illustrated in FIG. 1, filter 1 may include a hub 2, locator members 30, and anchor members 40 each of which preferably has a hook 43. A number of locator members 30 and anchor members 40 of the filter 1, which are sometimes referred to herein as filter members, are typically disposed approximately equiangularly about the hub 2, forming radial nets which catch and retain blood clots. The filter members can be made from a plurality of elongate wires, which are preferably metal, and more preferably are a super-elastic shape memory alloy, such as, for example, Nitinol. The shape memory alloy can further be defined as preferably having an austenite finish ($A_f$) temperature below body temperature. The wires are held together at the filter trailing end (with respect to the flow of blood through the filter) by hub 2 using a suitable connection technique, such as, for example, welding, laser welding, or plasma welding or being bonded together. Preferably, the wires are plasma welded. As used herein, "wire" refers to any elongated member of narrow cross section, including rods, bars, tubes, ribbon and narrow sections cut from thin plate, and is not intended to limit the scope of the invention to elongated members of circular cross section, cut from wire stock or manufactured according to a particular method of metal forming. Additional details on filter configurations and materials are disclosed in PCT International Application No. PCT/US06/017889, entitled "Removable Embolus Blood Clot Filter," filed May 9, 2006, which is hereby incorporated by reference in its entirety.

The locator members 30 may have a proximal end connected to hub 2 and a distal end referred to herein as the tip portion 35. Similarly, the anchor members 40 may have a proximal end 41 and a distal end 42. The anchor distal end 42 may be provided with hook 43, as shown in FIG. 1.

Figure 2:
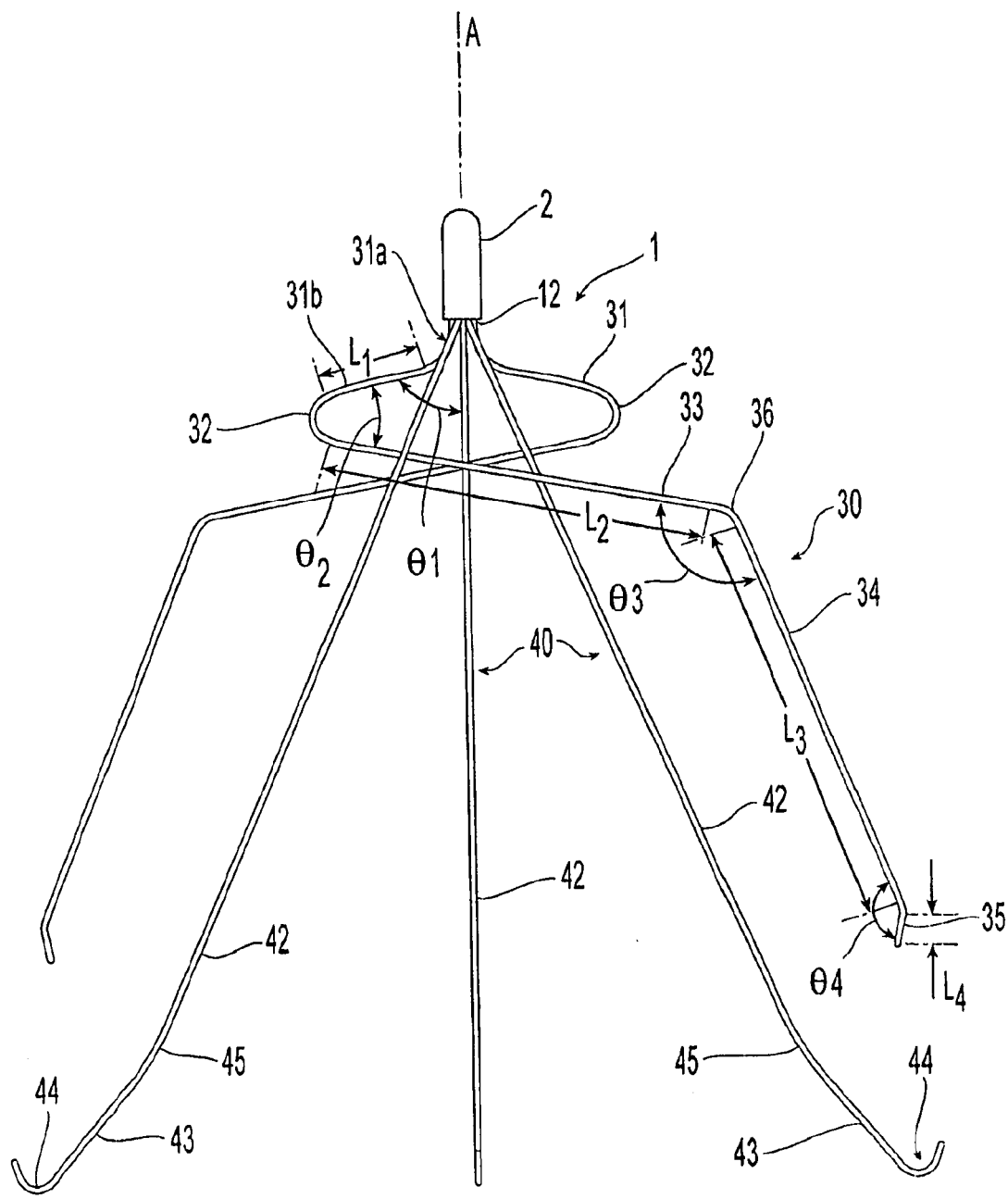
FIG. 2 is a perspective view of an embodiment of the blood filter of FIG. 1 after a bio-resorbable retainer has bio-absorbed.

A filter 1 according to the various embodiments may be delivered into a blood vessel of a subject by pushing it through and then out of a catheter positioned within the vein. The filter 1 may be stored in a storage tube in a compressed configuration with the filter members folded down along the centerline so that the filter can be pushed out of the storage tube and into the catheter, such as by a push wire: A filter 1 made from a super-elastic shape memory alloy, such as Nitinol, may be annealed during fabrication to attain a deployed shape (i.e., the memory shape), such as illustrated in FIG. 2, when at an elevated temperature, such as the subject's body temperature, and be elastic enough at lower temperatures to permit folding into a compressed configuration for storage and delivery via a catheter. Further details on the delivery of a blood filter 1 into a vessel are provided in PCT International Application No. PCT/US06/17890, entitled "Embolus Blood Clot Filter and Delivery System," filed on May 9, 2006, which is hereby incorporated by reference in its entirety.

Figure 3:
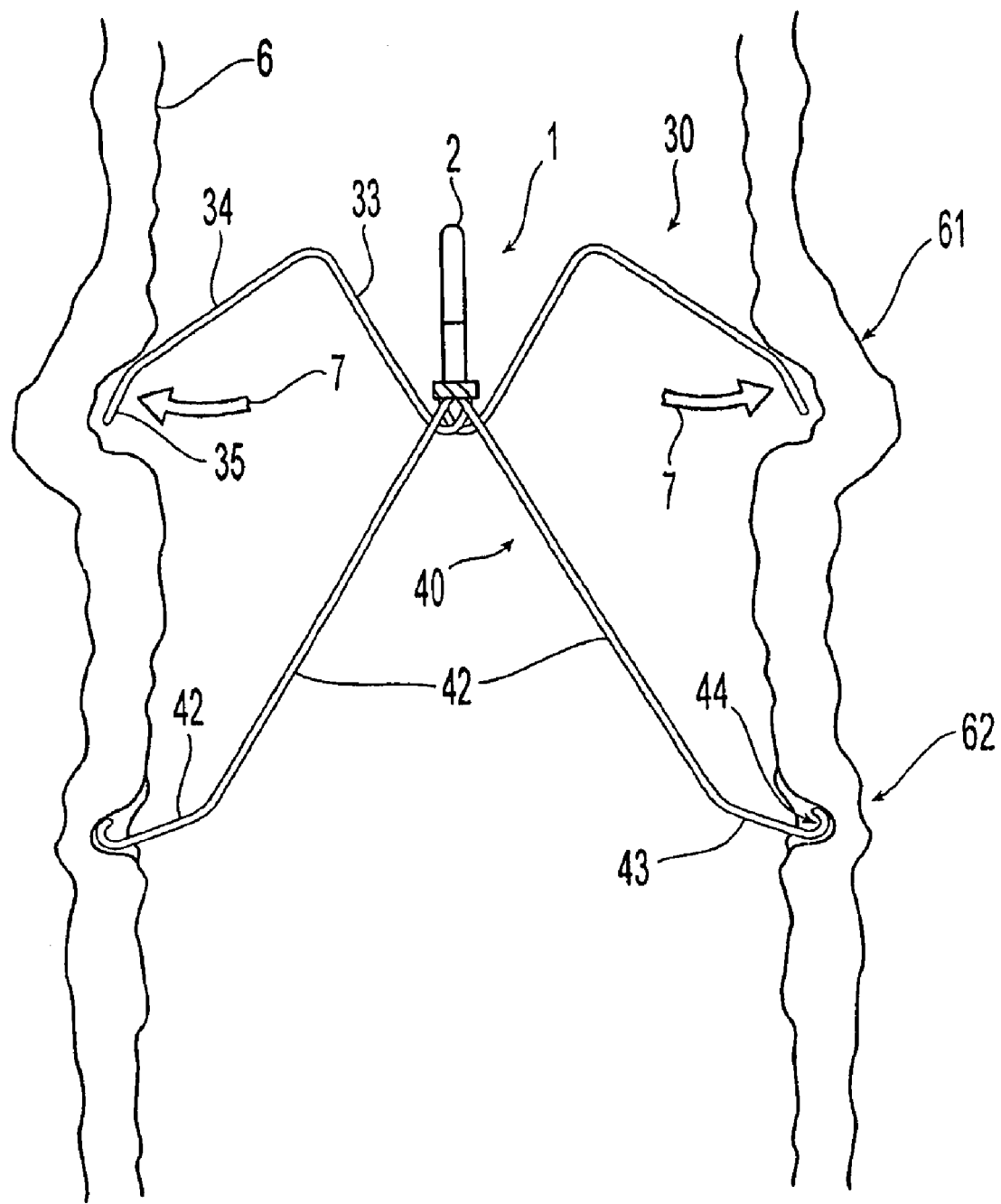
FIG. 3 is a plan view of the filter of FIG. 1 installed in a blood vessel.

To install a filter 1 within a blood vessel, it is important that the hub 2 be positioned approximately along the centerline of the blood vessel. To accomplish this, the filter locator members 30 may project radially from the hub 2 of the filter 1 so that when positioned within a blood vessel, the members apply radial pressure to the walls, thereby pushing the filter hub 2 toward the vessel centerline. This is illustrated in FIG. 3. When a filter 1, such as that illustrated in FIG. 1, is ejected into a blood vessel hub-end first from an insertion catheter, the locators 30 will deploy first. Since the as-deployed radial separation between locator tips is larger than the diameter of the blood vessel, the locator tips contact and push against the walls of the blood vessel, thereby centering the filter in the blood vessel before the anchor members 40 deploy from the delivery catheter. In addition to serving as filter elements for catching blood clots, this centering function is an important function of the locators. However, once the locators have centered the filter in the blood vessel and the anchor members have engaged the vessel walls, continued pressure against the vessel walls over the long term may cause damage to the vessel.

Similarly, the anchor members 40 may be configured so that when the filter 1 is delivered into a blood vessel, the anchors deploy radially so that the hooks 43 on the ends press against the walls of the vessel with sufficient force to drive the hook into the vessel wall. Once embedded in the vessel wall, the anchor hooks 43 prevent the filter from being dislodged by blood flow. While the radial pressure is necessary to engage the hooks with the vessel walls, after a few weeks the endothelial layer grows over the hooks. Thereafter, only a nominal (i.e., zero to small) radial force is necessary to maintain the engagement with the vessel walls, and any long term continued pressure against the vessel walls by the anchor members may damage the blood vessel.

To provide locator members 30 and anchor members 40 which perform the locating and anchoring functions until the filter is implanted, and then reduce the forces applied against the vessel walls, a bio-resorbable structure is used to constrain one or both of the members in an installation or first configuration which, after the material is resorbed in blood, changes to a second configuration characterized by reduced radial pressure. The bio-resorbable structure may be used to constrain a portion of the locator and anchor members, such as to limit their radial deployment. Alternatively, the bio-resorbable structure may be used to press filter members apart into a first configuration, such as to increase their radial displacement (i.e., increase the force applied to the vessel walls), which later relaxes to a second configuration when the structure is resorbed. In a third alternative, the bio-resorbable structure may reinforce or otherwise increase the rigidity of a portion of the locator and anchor members so that the members assume a first configuration which presses against the vessel wall due to their configuration and elasticity, which later relaxes to a second configuration when the reinforcing structure is resorbed. A number of alternative embodiments of filter members and bio-resorbable structures are contemplated, illustrative examples of which are described with reference to the figures.

Materials which bio-resorb in blood and are assimilated by the body (i.e., absorbed) at predictable rates are well known in the medical arts and used in a variety of applications. For example, bio-resorbable sutures and staples are commonly used in surgical procedures to close internal wounds long enough to permit tissues to heal before bio-absorbing away to reduce the potential for foreign object rejection and infections. A number of materials are used for bio-resorbable sutures and may be used for the bio-resorbable structures of the various embodiments. Such materials may be made from natural materials or synthetic polymers. Natural bio-resorbable materials include, but are not limited to, natural collagens, submucosa sheep intestine, plain gut serosa of beef intestine, and collagen beef flexor tendon. Natural absorbable materials prepared from mucosa or submucosa sheep or beef intestines are broken down by enzymatic degradation within the cell. Synthetic bio-resorbable materials include, but are not limited to: Polyglycolic acid Dexon S homopolymer of glycolic acid; Polyglycolic acid Dexon plus homopolymer of glycolic acid coated with poloxamer 188; Polyglycolic acid Dexon II homopolymer of glycolic acid coated with polycaprolate; Polyglactine 910 Vicryl copolymer lactideglycolic acid coated with calcium stearate; Polydioxanone PDS polymer of paradioxanone; Polydioxanone PDS-II modified PDS; Polyglyconate Maxon copolymer of trimethylene carbonate and polyglycolicacid; and, Polyglecaprone 25 Monocryl copolymer of e-caprolactone and glycolide. Synthetic bio-resorbable materials are first hydrolyzed (hydrolytic degradation) and then metabolized by the cell. Once the bio-resorbable material has been degraded by hydrolysis the fragments are phagocytized by the enzymatic action of the cells, metabolized and excreted. The bio-resorbable materials can be configured to be absorbed or degraded from 2 weeks to 2 years. Other materials can include biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol), polycaprolactone (available commercially as Capronor), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanoacrylates, or polyphosphazenes. As used herein, the term "bio-resorbable" includes a suitable bio-compatible material, mixture of materials or partial components of materials being degraded into other generally non-toxic materials by an agent present in biological tissue (i.e., being biodegradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable materials noted above.

Two factors determine the rate of hydrolysis of synthetic bio-resorbable materials; the molecular weight and morphology of the polymer. Thus, by selecting among the available bio-resorbable materials and setting the thickness of the structure, the endurance of the bio-resorbable structure (i.e., the time in the body before the material fails under the loads applied by filter members) can be controlled. Additionally, hydrolytic degradation can be delayed by coating the surface of the bio-resorbable structure, such as with a hydrophobic layer formed of, for example, a copolymer of lactide, glactide and calcium stearate, which forms an absorbable, adherent, non-flaking lubricant which repels water and slows absorption, thereby improving retention of tensile strength. Additionally, the coating may be of a chemical structure that degrades, such as by breaking polymer chains to increase porosity, when exposed to sufficiently energetic radiation, such as ultraviolet light.

Figure 4:
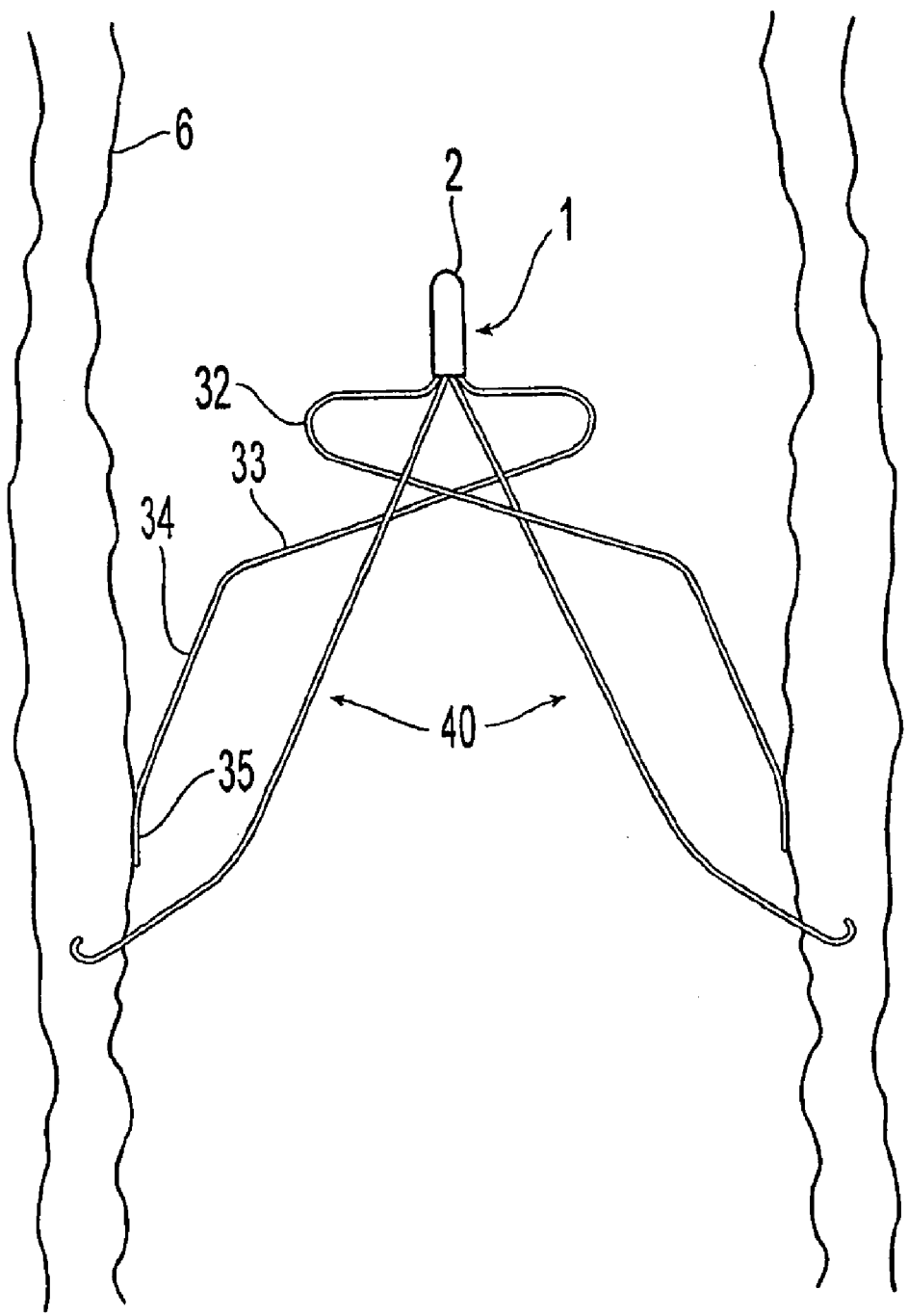
FIG. 4 is a plan view of the filter of FIG. 1 installed in a blood vessel after the bio-resorbable retainer has bio-absorbed.

In the embodiment illustrated in FIGS. 1-4, the locator members 30 include a recurved portion 31, extending from the hub 2, which couples to a linear second portion 32 which couples to a linear third portion 34 which couples to a tip portion 35. In alternative embodiments, the linear second portion 32 and the linear third portion 34 may have a single curvilinear portion, and thus these portions are also referred to herein as an extended portion of the locators. Prior to delivery into a blood vessel, such as during assembly of the filter 1 in a storage tube, a bio-resorbable retainer 50 (FIG. 1) may be used to constrain (i.e., bend) the recurved portion 31 of the locator 30 into a first configuration so that the second portion 33 and third portion 34 (together the extended portion) are deployed radially. Due to the recurved shape of the recurved portion 31 and the angles $\theta_1$ and $\theta_2$ at the joints or bends 32, 36 connecting recurved portion 31 to the second portion 33, and the second portion 33 to the third portion 34, respectively, when the recurved portions are constrained (e.g., wrapped) by the bio-resorbable retainer 50 into the first configuration illustrated in FIG. 1, the tip portions 35 of the locator members 30 are positioned at a greater distance from the centerline of the filter than when the bio-resorbable retainer 50 is removed and the recurved portions 31 return to their normal shape, which is the second configuration illustrated in FIG. 2. The locator members are preferably made of a resilient spring material, such as Nitinol or Eligiloy®, so that the recurved portions 31 preferably provides a spring portion 31 to the locator 30 that can be bent into the constrained (i.e., first) configuration shown in FIGS. 1 and 3 and return to their unconstrained (i.e., second) configuration after the restraint is removed, as shown in FIGS. 2 and 4. The flexible nature of the locator members 30 also permits the members to flex as they press against the vessel walls to apply an even force and avoid damage to the walls.

Each locator members' recurved segment 31 may be distinct from locator first segment 33 by virtue of a joint or bend 32. In addition, the locator first segment 33 may be distinct from locator second segment 34 via a joint or bend 36. The joint or bend 32 or 36 can be viewed as a location formed by the intersection of the segments defining a radiused portion connecting any two segments. The filter 1 may have a number of locators 30 preferably ranging from 2 to 12. The filter embodiment illustrated in FIGS. 1-4 illustrate only two, but the filter may preferably include three, four, six or any number of locators (generally greater than three) which are preferably equiangularly spaced about the longitudinal axis of the filter.

Referring to FIG. 2, the recurved portion 31 may be characterized by a first curve 31*a* or bend through angle $\theta_1$ with respect to the centerline A of the filter 1, the length of a generally (though not necessarily) straight portion 31*b*, and the angle $\theta_2$ of joint or bend 32 which is preferably defined by the angular relation between the straight portion 31*b* and the first segment 33. Thus, the larger the angle $\theta_1$ and the longer the straight portion 31*b*, the greater the movement of the tip portion 35 of the locator member 30 during actuation.

As illustrated in FIG. 3, when this embodiment filter 1 is installed in a blood vessel, the radial deployment of the locators 30 due to the constrained position imposed by the bio-resorbable material 50 causes the tip portions 35 to press against the vessel wall 6 with a first radial force 7. This first force 7 causes the filter 1 to center itself generally equidistant from the vessel walls 6. This force 7 may also cause distortion 61 of the vessel wall. In some configurations, part or the entire second segment 34 may also press against the vessel walls as the locator members 30 flex under the applied force.

After a period of time, such as a few days to several weeks, and typically less than 60 days, the bio-resorbable material 50 is sufficiently weakened by enzymatic or hydrolytic degradation that the restraint breaks, releasing the restraint on the recurved portion 31. So released, the recurved portions 31 return to their unconstrained (i.e., second) configurations, moving radially outward which causes the tip 35 of the locator members 30 to move radially inward, as illustrated in FIGS. 2 and 4. In this configuration, the pressure asserted by the locator members against the vessel walls 6 is reduced due to a second radial force less than the first radial force.

Locator members 30 for the filter embodiment illustrated in FIGS. 1-4 are characterized by a number of design parameters which can be adjusted in order to configure the filter for a particular application and target blood vessel. In particular, design parameters may be selected in order to define the first and second configurations of the filter members. As shown in FIG. 2, these design parameters include the lengths $L_1, L_2, L_3$ and $L_4$ of recurved portion 31*b*, first segment 33, second segment 34 and tip portion 35, respectively, and angles $\theta_1, \theta_2$ and $\theta_3$ of first curve 31*a* and joints or bends 32 and 36, respectively. Joint or bend 32 connects the recurved portion 31 to the first segment 33, and joint or bend 36 connects the first segment 33 to the second segment 34.

As will be appreciated by one of skill in the art, the thickness of the various locator member segments may also be adjusted in order to control the force applied by displacement (i.e., flexing) of the portions when in contact with a vessel wall. The radial diameter of the deployed locator members 30 (i.e., effective diameter of the locator member portion of the filter), both in the restrained (i.e., first, just after delivery) and unrestrained (i.e., second, after absorption of the restraint) configurations, can be controlled by adjusting any one or all of the design parameters noted above. Additionally, the amount of actuation movement (i.e., the movement that occurs when the restraint is resorbed) can be controlled by adjusting angle $\theta_1$ and the length $L_1$ of the straight portion 31*b* of the recurved portion 31. Similarly, the path that the tip 35 follows during actuation may be controlled by modifying any combination of these design parameters. Thus, these design parameters enable one skilled in the art to configure a filter to meet particular needs of a specific application, such as a filter for a particular blood vessel, a desired maximum and minimum centering force and a desired orientation after actuation.

By way of example, but not by way of limitation, locator members 30 of a filter 1 according to this embodiment may have the characteristic dimensions listed below in Table 1.

TABLE 1

| Parameter | Range of Values | Preferred Range |
|---|---|---|
| $\theta_1$ | About 1° to about 90° | About 10° to about 30° |
| $\theta_2$ | About 20° to about 120° | About 20° to about 90° |
| $\theta_3$ | About 80° to about 170° | About 90° to about 135° |
| $\theta_4$ | About 90° to about 170° | About 150° to about 170° |
| $L_1$ | About 0.1 inch to about 0.5 inch | About 0.2 inch to about 0.3 inch |
| $L_2$ | About 0.2 inch to about 1.0 inch | About 0.4 inch to about 0.6 inch |
| $L_3$ | About 0.2 inch to about 1.0 inch | About 0.4 inch to about 0.6 inch |
| $L_4$ | About 0 inch to about 0.3 inch | About 0.1 inch to about 0.25 inch |

Figure 5A:
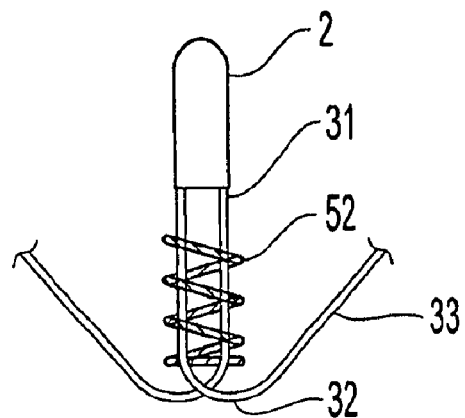
FIG. 5A is a detailed view of an alternative embodiment of the bio-resorbable retainer of the filter of FIG. 1.
Figure 5B:
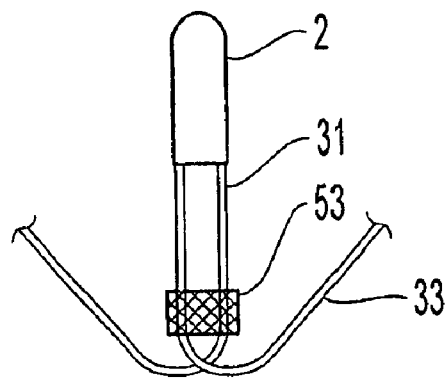
FIG. 5B is a detailed view of another alternative embodiment of the bio-resorbable retainer of the filter of FIG. 1.
Figure 5C:
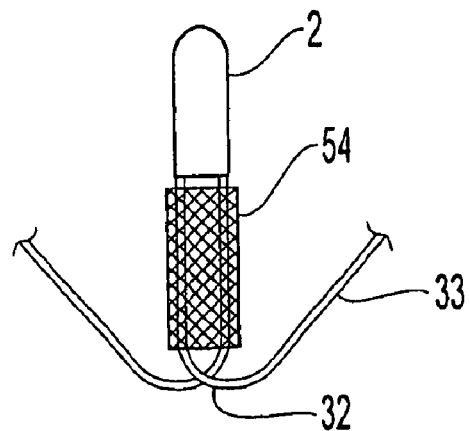
FIG. 5C is detailed view of another alternative embodiment of the bio-resorbable retainer of the filter of FIG. 1.

A number of different configurations for the bio-resorbable restraint are contemplated as part of the various embodiments. For example, FIGS. 5A-5C illustrate three example alternatives. However, any configuration or use of bio-resorbable structure to enable post-delivery actuation of locator members 30 is contemplated as part of the various embodiments.

Referring to FIG. 5A, the bio-resorbable restraint may be in the form of a thread or suture 52 wrapped about the recurved portion 31 of the locator member 30. This embodiment has the advantage of using commercially available bio-resorbable sutures. The thickness of the suture (i.e., the size of the cross section of the bio-resorbable material) can be modified to control the deployment of the locator. It is believed that a controlled actuation according to this embodiment may prevent or reduce the potential for injury to blood vessel walls. Varying the number of wraps may also be useful for controlling the deployment of the locators.

Referring to FIG. 5B, the restraint may be in the form of a band 53 or bands (such as are illustrated in FIG. 1). In this embodiment, the restraint may be prefabricated as a single band 53 of wholly or partially resorbable material or a coil of bio-resorbable suture. Such a band 53 may be sized to slip over the hub and to be pressed down over the recurved portion 31 of the locator members 30 during fabrication, thereby obviating the need for an assembly step involving wrapping the filter members as described above with reference to FIG. 5A. In the alternative where a number of bands 50 are employed, as illustrated in FIG. 1, the bands may be sized such that a thinner band is positioned close to the bend 32, while progressively thicker bands are employed closer to the hub 2. This alternative will enable a progressive deployment of the locator members 30 from a first configuration to a second configuration similar to that described above with respect to FIG. 5A, since thinner bands will generally fail before thicker bands. As such, the locator members 30 will deploy (i.e., move from the first configuration to the second configuration) slowly. Also, multiple bands may permit the filter members to assume one or more intermediate configurations between the first and second configurations, controlled in form and duration by the nature, position and size of the intermediate restraint structure. In another alternative, the band 53 may include a lubricating surface or be configured to receive lubrication from blood so that it is able to slide toward the hub 2, thereby allowing the locator members 30 to partially deploy (such as into an intermediate configuration) soon after delivery.

In a further alternative, the band 53 is not resorbable, but the portion connecting the band 53 to the filter is resorbable. In this embodiment, the band 53, possibly in conjunction with lubricant, will slide towards the hub 2 when the resorbable connector breaks or is resorbed. This embodiment is believed to be advantageous in that no substantial piece of resorbable material is released or permitted to float freely in the blood vessel since the band remains on the filter.

Figure 6:
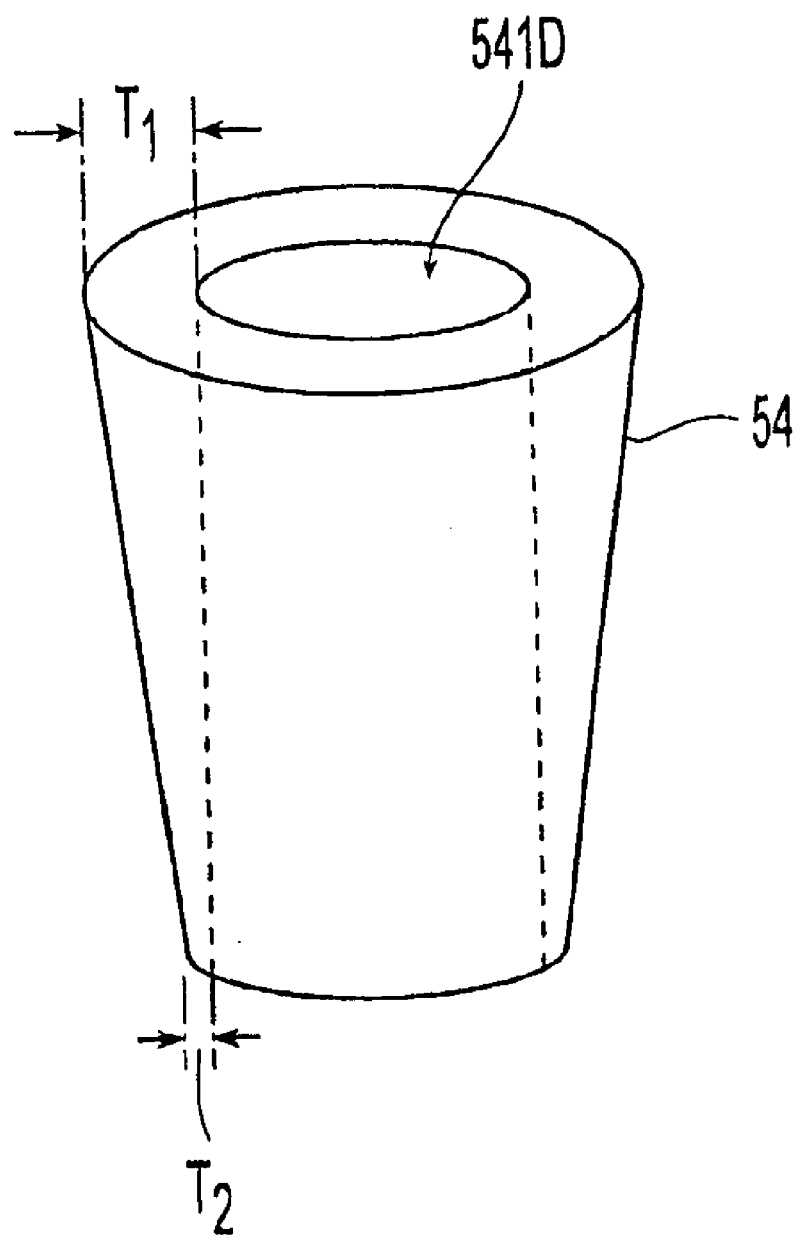
FIG. 6 is a detailed view of another alternative embodiment of a bio-resorbable retainer.

Referring to FIG. 5C, the constraint may also be in the form of a sleeve 54 fitting over an extended portion of the recurved members 31. Such a sleeve 54 may be prefabricated as a single band or cylinder 54 of a wholly or partially resorbable material or a cylinder of coiled bio-resorbable suture. Such a sleeve 54 may be sized to slip over the hub and to be pressed down over the recurved portion 31 of the locator members 30 during fabrication, thereby obviating the need for an assembly step involving wrapping the filter members as described above with reference to FIG. 5A. Since the force applied by the recurved portion 31 is greater near the bend 32 than near the hub 2 due to the lever effect, a sleeve 54 will tend to tear progressively, thereby allowing a controlled or progressive deployment of the locator members 30 from their first configuration to their second configuration. Alternatively, the sleeve 54 may be fabricated with a variable cross section, such as employing bands of increased thickness or a linear taper such as illustrated in FIG. 6. The sleeve 54 illustrated in FIG. 6 preferably defines a constant inner diameter 54IID and a tapering outer surface so as to define a sleeve wall thickness generally linearly tapering from one end with thickness $T_1$ to an opposite axial end having a thickness $T_2$. The sleeve may be slipped over the recurved portion 31 during fabrication so that the thin cross section portion $T_2$ is close to the bend 32. The variable thickness of the sleeve 54 illustrated in FIG. 6 enables the locator members to deploy progressively, since the thin cross section portion will fail before the thicker portion.

Referring to FIG. 5D, the first segment 33 can be provided with a variable stiffness hinge. Specifically, a hinge 33A formed by a smaller generally constant cross section of the first segment 33 is covered with bioresorbable material 50. Before the bio-resorbable material 50 is resorbed, the segment 33 with hinge 33A remains of a generally constant stiffness throughout its length. Upon resorbtion, however, the segment has at least two distinct regions of different stiffness. Instead of a constant smaller cross section, a hinge 33B formed by varying smaller cross sections can be provided, as shown in FIG. 5E. Additional details of the hinge are shown and described in U.S. Pat. No. 5,776,162, which is hereby incorporated by reference in its entirety. Alternatively, a helical coil spring can be used instead of hinge 33A or 33B. The bio-resorbable material 50 can cover the outside of such helical spring or be provided on the inside of the helical coil spring.

Referring to FIG. 5F, instead of bio-resorbable bands, a combination of a non-resorbable sleeve 54A and resorbable material 50 can be utilized. In this embodiment, the hub 2 (as shown in, for example, FIG. 1) is optional as the plurality of first segments 33 can be bonded or welded together to act as a hub. In such case, the bioresorbable material 50 directly covers the plurality of segments 33 while preventing the non-resorbable sleeve 54A from moving upward on the segments as displayed in FIG. 5F. The sleeve 54A can be made of any suitable material, including metals coated with a suitable bio-compatible material such as, for example, PTFE to reduce friction. To aid the sleeve in moving upward on the segments as displayed in FIG. 5F, the internal surface of the sleeve 54A can be configured in the form of a cone whose smallest inside diameter is substantially larger than the diameter of the outer boundary defined by the segments.

Figure 7A:
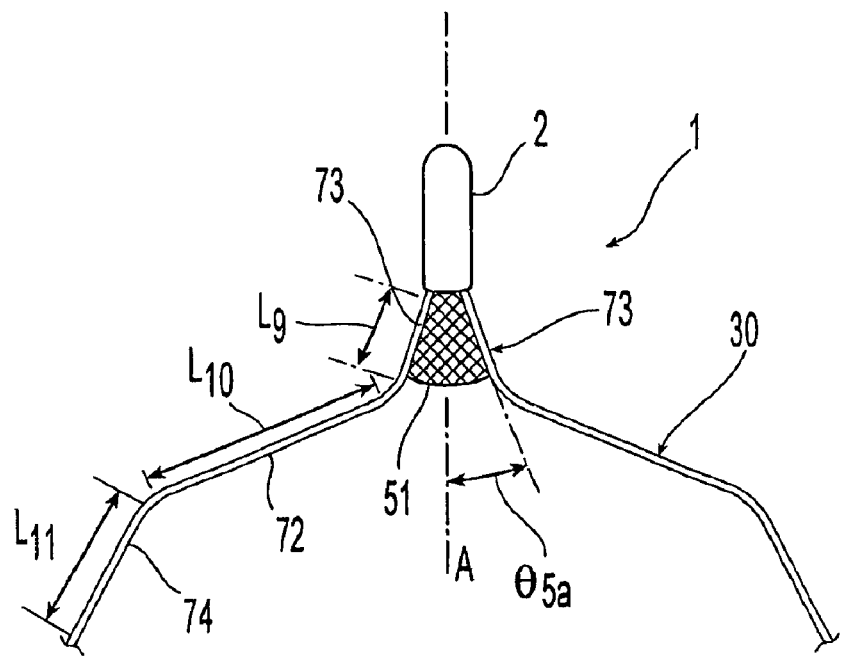
FIG. 7A is a detailed view of an alternative embodiment of the filter of FIG. 1 including a bio-resorbable displacement wedge.

In another embodiment, bio-resorbable structure may be employed to displace a portion of the locator members 30 in order to increase their radial deployment in a first configuration. As illustrated in FIG. 7A, such a bio-resorbable displacement structure 51 may be a plug, bead, cone (illustrated) or wedge of bio-resorbable material that is positioned between a first portion 73 of the locator members 30. Positioned near the hub 2, a displacement structure 51 can cause a relatively large change in the radial deployment of the locator members 30 depending upon the length of the locator members 30 and the angle between the first portion 73 and rest of the locator member 30.

Figure 7B:
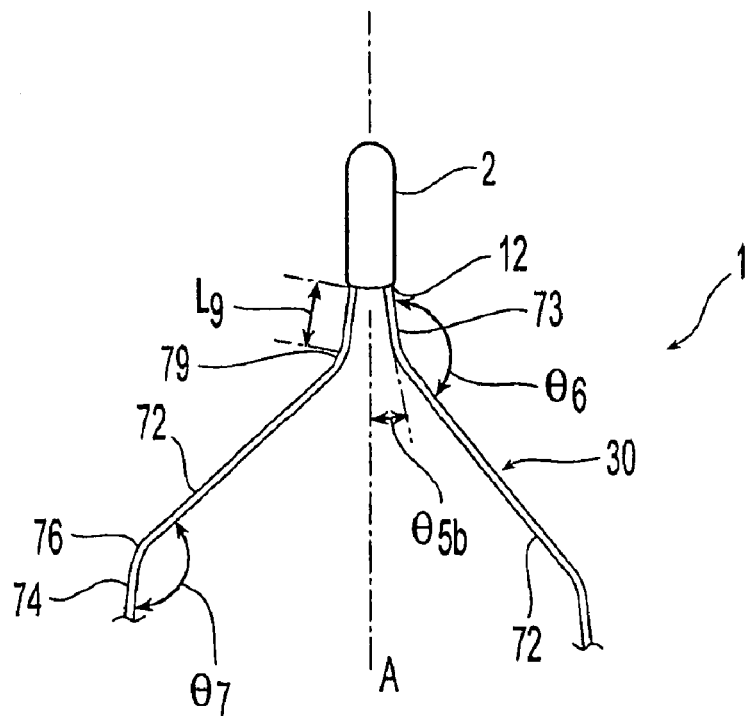
FIG. 7B is a detailed view of an alternative embodiment of the filter of FIG. 7A after the displacement wedge has bio-adsorbed.
Figure 7C:
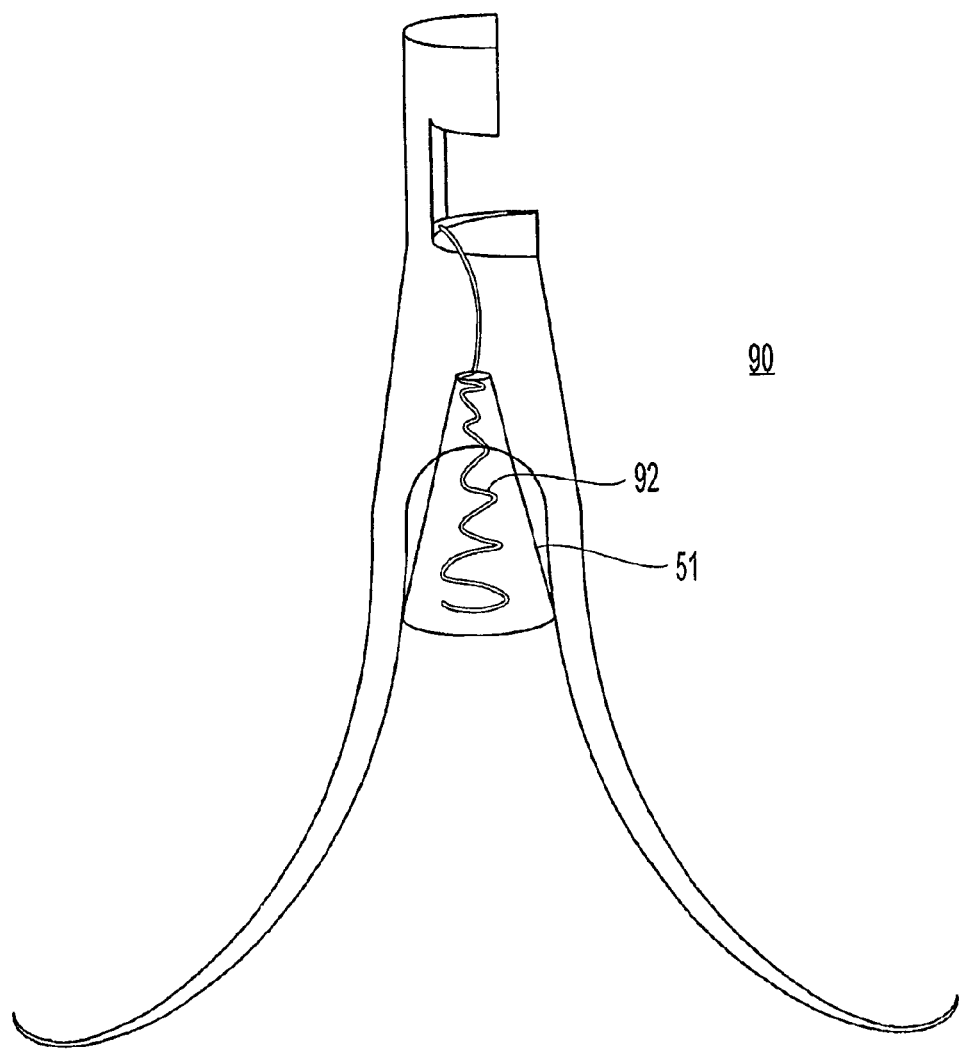
FIG. 7C illustrates an alternative embodiment of a filter employing bio-resorbable material.

After delivery, the bio-resorbable displacement structure will eventually degrade and finally be resorbed by the body, allowing the first portion 73 to return to its stress-free, second configuration, thereby moving the tips of the locator members toward the filter centerline and decreasing angle at which the locator members project from the longitudinal axis from initially $\theta_{5a}$ to $\theta_{5b}$, as illustrated in FIGS. 7A and 7B. The displacement structure 51 can also be utilized in a filter 90 formed from a hollow tube stock such as illustrated in FIG. 7C. The structure of the filter 90 can be cut out of a stock using a suitable technique (e.g., laser or chemical etching) to form the generally cylindrical hub and anchor segments. The displacement structure 51 can be coupled at a region where the anchors join to the hub body. To reduce the fracturing of bioresorbable material 51 during resorbtion in the host, a coil spring 92 can be connected to the filter 90 so as to form a back bone to which the material 51 can attach.

Figure 7D:
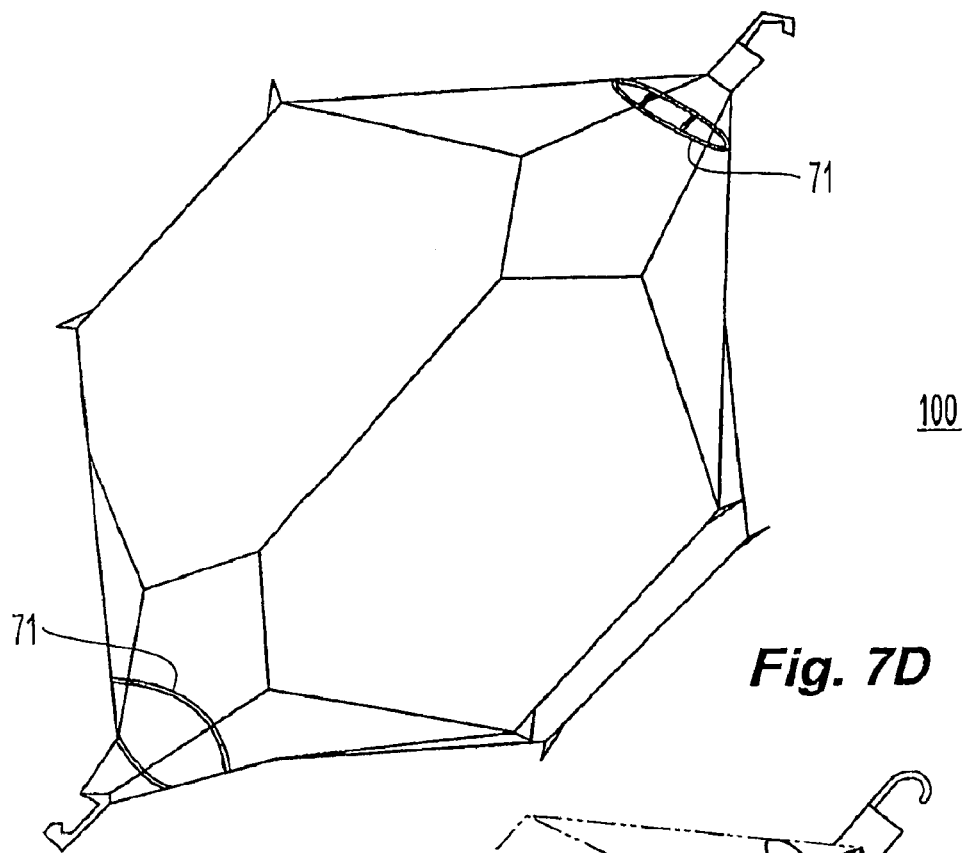
FIGS. 7D and 7E illustrate an alternative embodiment of a filter employing bio-resorbable material.
Figure 7E:
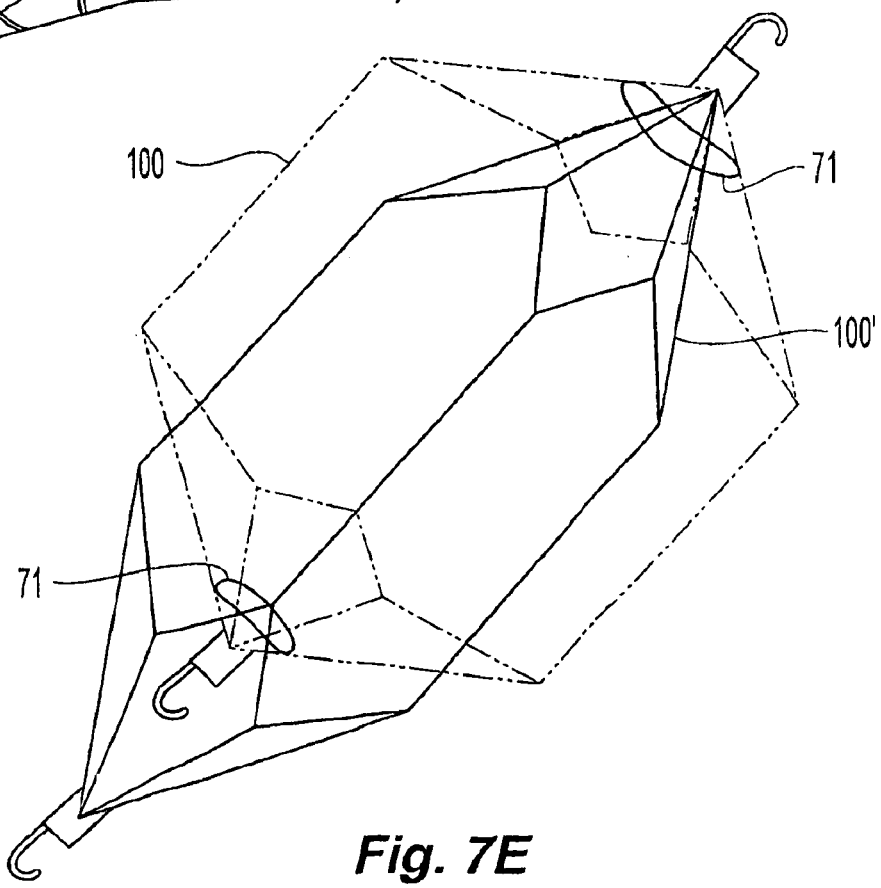

The feature of increasing radial deployment force at initial implantation can also be applied to other filters. For example, in FIG. 7D, a commercially available filter 100 (OptEase®/TrapEase®) can be provided with a generally conical plug 71 at both ends. During initial deployment, the plugs 71 cause the filter 100 to be oversized (shown by dashed lines in FIG. 7E). Upon resorbtion of plugs 71, the filter reconfigures to a longer, smaller diameter filter 100' (shown by solid lines). Hence, where the vessel diameter is 28 mm, a filter can be selected to have an initial oversize diameter configuration of about 40 mm with a smaller diameter configuration filter between 28 mm and 40 mm.

Figure 8A:
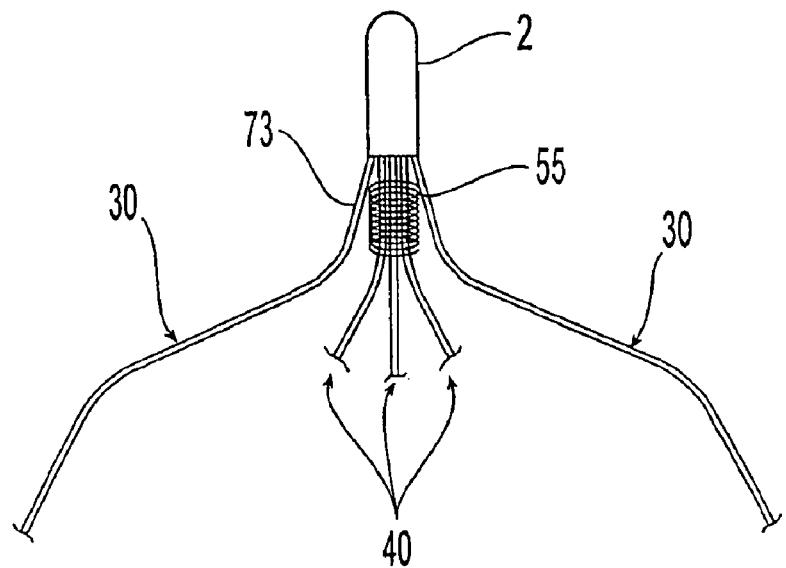
FIG. 8A is a detailed view of an alternative embodiment of the filter of FIG. 1 including bio-resorbable displacement wraps.
Figure 8B:
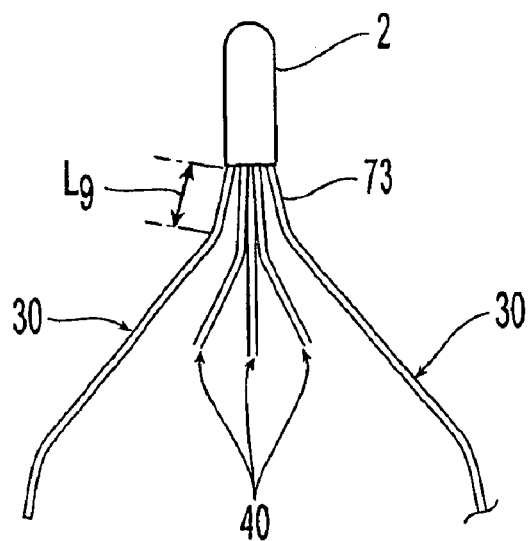
FIG. 8B is a detailed view of an alternative embodiment of the filter of FIG. 8A after the displacement wraps have bio-absorbed.

In an alternative embodiment illustrated in FIG. 8A, the displacement structure may be in the form of a number of bio-resorbable bands or wraps 55, such as wraps of bio-resorbable suture, positioned around a portion of the anchor members 40. In this embodiment, the bands or wraps 55 radially displace the first portion 73 of the locator members into a first configuration, resulting in a wider initial deployment of the locator members, as illustrated in FIG. 8A. After delivery, the bio-resorbable displacement structure will eventually resorb, allowing the first portion 73 to return to its stress-free, second configuration, thereby moving the tips of the locator members toward the filter centerline, as illustrated in FIG. 8B.

Locator members for the filter embodiment illustrated in FIGS. 7A, 7B, 8A, and 8B are characterized by a number of design parameters which can be adjusted in order to configure the filter for a particular application and target blood vessel. Referring to FIGS. 7A and 7B, these design parameters include the lengths $L_9$ of the first portion 73, $L_{10}$ of the second portion 72, $L_{11}$ of the third portion 74 and $L_{12}$ of the tip portion 75 (not shown), the angles $\theta_{5a}$ and $\theta_{5b}$ of the first portion 73 to the centerline A of the filter 1, the angle $\theta_6$ of the joint or bend 79 connecting the first portion 73 to the second portion 72, and the angle $\theta_7$ of the joint or bend 76 connecting the second portion 72 to the third portion 74. Additionally, the thickness of the various locator member portions may be adjusted in order to control the force applied by an amount of displacement (i.e., flexing) of the portions when in contact with a vessel wall. As will be appreciated by one of skill in the art, the radial diameter of the deployed locator members 30 (i.e., effective diameter of the locator member portion of the filter), both in the restrained (i.e., first, just after delivery) configuration and unrestrained (i.e., second, after dissolution of the restraint), can be controlled by adjusting any one or all of these design parameters. Additionally, the amount of actuation movement (i.e., the movement that occurs when the restraint is resorbed) can be controlled by adjusting the size of the displacement structure to determine the change from the angle $\theta_{5a}$ of the first portion 73 with respect to the filter centerline A in the as-delivered state to the angle $\theta_{5b}$ after the displacement structure has bio-absorbed away, as well as the overall length of the locator member 30. Angle $\theta_8$ (not shown), of the joint connecting third portion 74 to tip portion 75 may also be adjusted as desired. Thus, these design parameters enable one of skill in the art to configure a filter to meet particular needs of a specific application, such as a filter for a particular blood vessel, a desired maximum and minimum centering force in a first configuration and a desired orientation after actuation into a second configuration.

By way of example, but not by way of limitation, locator members 30 of a filter 1 according to the embodiment shown in FIGS. 7A, 7B, 8A, and 8B may have the characteristic dimensions listed below in Table 2.

TABLE 2

| Parameter | Range of Values | Preferred Range |
|---|---|---|
| $\theta_{5a}$ | About 1° to about 45° | About 10° to about 30° |
| $\theta_{5b}$ | About 0° to about 40° | About 5° to about 20° |
| $\theta_6$ | About 20° to about 90° | About 30° to about 45° |
| $\theta_7$ | About 90° to about 170° | About 110° to about 135° |
| $\theta_8$ | About 90° to about 170° | About 150° to about 170° |
| $L_9$ | About 0.1 inch to about 0.8 inch | About 0.2 inch to about 0.4 inch |
| $L_{10}$ | About 0.2 inch to about 1.0 inch | About 0.4 inch to about 0.6 inch |
| $L_{11}$ | About 0.2 inch to about 1.0 inch | About 0.4 inch to about 0.6 inch |
| $L_{12}$ | About 0 inch to about 0.3 inch | About 0.1 inch to about 0.25 inch |

The amount of actuation (e.g., change in radial deployment) and force initially applied against vessel walls may be adjusted by configuring the volume of the displacement structure and the component angles and lengths of the locator members 30. For example, relatively small actuation may be provided by employing a small displacement structure.

While bio-resorbable displacement structure embodiments illustrated in FIGS. 7A-B and 8A-B may exhibit a smaller range of actuation motion, those embodiments may be preferred for some applications over the recurved locator member embodiments illustrated in FIGS. 1-4. For example, the movement of the locator members 30 with the displacement structure embodiment is strictly radially inward, which may place less stress upon the vessel walls. In contrast, the movement of the locator member tips 35 in the embodiments illustrated in FIGS. 1-4 may be down (i.e., longitudinally away from the hub 2) and inward (i.e., toward the centerline). Depending upon the application, one deployment movement and range of motion may be preferred over the other. Additionally, the bio-resorbable displacement structure embodiments may be preferred for filters designed to be readily removable since the locator members 30 may be more easily collapsed into a retraction catheter than would be the case for the recurved locator member embodiments shown in FIGS. 1-4.

For the locator actuating embodiments described above with reference to FIGS. 1-7B and 8A-8B, any of a number of alternative configurations of anchor members 40 may be employed. For example, a filter 1 may employ anchors similar to those described in U.S. Pat. No. 6,258,026, or in PCT International Application No. PCT/US06/017889, entitled "Removable Embolus Blood Clot Filter," both of which are hereby incorporated by reference in their entirety. An example of a suitable anchor member will now be described with reference to FIGS. 1 and 2. Each of the plurality of anchor members 40 may be provided with a first anchor segment 41, a portion of which may be disposed within the hub 2, connected to a second anchor segment 42 by a joint or bend (not shown), which may be connected to a third anchor segment 43 via joint or bend 45. The third anchor segment 43 may be connected to a hook 44 via third anchor joint or bend (also not shown). The first anchor segment 41 extends obliquely with respect to axis A. The second anchor segment 42 extends for a length $L_5$ along axis 46 oblique with respect to the axis A over an angle $\theta_9$ with respect to the longitudinal axis A. The third anchor segment 43 extends length $L_6$ along axis 47 oblique with respect to the longitudinal axis A over an angle $\theta_{10}$. The anchor joint or bend 45 can be located at a sixth longitudinal distance $L_7$ as measured on an axis generally parallel to the axis A from the terminal surface 12 of the hub 2 and at about one-half the diameter D1 as measured between generally diametrical end points of two anchors 40 on an axis generally orthogonal to the axis A. The thickness of anchor member 40 is nominally $T_3$. Where the anchor member 40 is preferably a wire of circular cross section, the thickness $T_3$ of the anchor 40 may be the diameter of the wire.

Hook 44 may be located generally at a longitudinal distance LB as measured along an axis generally parallel to axis A and at a transverse distance of about one-half diameter D2 as measured on an axis orthogonal to the axis A between the inner surfaces of two generally diametric anchors 40. The hook 44 may be characterized by a thickness $T_4$ and a radius of curvature $R_1$, in its expanded configuration at a suitable temperature, e.g., room temperature or the internal temperature of a subject. The center of the hook curvature R1 may be located at a distance $L_8$-$R_1$ as measured along an axis generally parallel to the axis A from the terminal surface 12 of hub 2 and at approximately one-half diameter D2 as measured between two generally diametrical hooks 44.

A range of values may be used for the aforementioned dimensional parameters in order to provide anchor members 40 that will locate and anchor the filter 1 within the vein or vessel such that the hooks 44 contact the walls of the vein or vessel and provide sufficient lateral force against the vein or vessel wall to ensure the hooks engage the wall but not so much force as to injure the wall. For example, a filter intended to be placed in a narrow vein or vessel, such as a child or canine vena cava, may have smaller dimensions than a filter intended to be placed in a large vein or vessels, such as an adult vena cava or femoral vein to facilitate adequate deployment of the anchor members so as to accomplish the positioning, anchoring and filtering functions. In an example embodiment suitable for an adult human vena cava filter, when the filter is at the temperature of the subject and unconstrained, the length of the first portion 41 may be about 0.02 inches, the longitudinal distance $L_8$ may be about 1.3 inches; D2 may be about 1.5 inches; D2 may be between 1.5 and 1.6 inches; the radius of curvature $R_1$ may be about 0.03 inches; and the thickness $T_3$ of the anchor member may be about 0.013 inches.

The hook 44 may be formed to have a thickness $T_4$. Where the hook 40 is formed from a wire having a generally circular cross-section, the thickness $T_4$ may be generally equal to the outside diameter of the wire. In an embodiment, the hook thickness $T_4$ is less than and preferably approximately 60%-80% that of the anchor thickness T3. The thinner cross section of the hook 44 is provided so that when a force is applied, such as a retraction force, the anchor member 40 preferentially changes the radius of curvature of the hook 44, thereby reducing damage to the blood vessel walls.

The anchor members 40 form a sieve which is the primary filter element and can comprise up to twelve circumferentially spaced anchor members 40. The anchor members may be of equal length, but may alternatively or in addition to be of different lengths so that the hooks 44 at the ends of the wires will fit within a delivery catheter without becoming interconnected. The anchor members 40, in their expanded configuration illustrated in FIGS. 1 and 3, are at a slight angle to the vessel wall 6, preferably within a range of from ten to forty-five degrees, while the hooks 44 penetrate the vessel wall 6 to anchor the filter 1 against longitudinal movement. The anchor members 40 may be radially offset about the filter centerline A relative to the locator members 30 and may be positioned radially halfway between the locator members 30 and also may be circumferentially spaced by sixty degrees of arc.

The locator members 30 form another sieve. Thus, the combined filter sieves of the anchor and locator members can provide a wire positioned radially about the hub 2, such as at every thirty degrees of arc at the maximum divergence of the filter sections. Further, hooks may be provided on the tips of the locator members to further prevent migration of the filter in the blood vessel.

The structure of the hooks 44 is believed to be important in resisting migration of the filter 1 once installed while allowing for potential removal from the blood vessel 6 after installation. As in the case of hooks formed on the anchor members of known permanent vena cava filters, these hooks 44 penetrate the vessel wall when the filter 1 is expanded to anchor the filter in place and prevent longitudinal migration within the vessel in either direction.

To permit safe removal of the filter, the hooks 44 may be considerably reduced in thickness $T_4$ or cross section relative to the thickness $T_3$ or cross section of the anchor member 40. The hook thickness $T_4$ may be selected such that it is of sufficient stiffness when the anchor members 40 are expanded to permit the hook 44 to penetrate the vena cava wall. Preferably, however, when the hook is to be withdrawn from the vessel wall, withdrawal force in the direction of blood flow will cause flexure in the hook so that the hook tip moves toward a position parallel with the axis A (i.e., the hook straightens). With the hooks so straightened, the filter can be withdrawn without tearing the vessel wall while leaving only small punctures. In an embodiment, the anchor member 40 has a cross sectional area of about 0.00013 squared inches, and the hook 44 has a cross sectional area of about 0.000086 squared inches.

In a preferred embodiment, a bio-resorbable structure is employed with the anchor members 40 in order to enable their actuation after delivery, such as repositioning from a first configuration upon delivery to a second configuration after the hooks on the ends of the anchors are embedded in the blood vessel characterized by reduced force applied to vessel walls. Such a filter may employ non-actuating locator members typical of known filters, as is illustrated in FIG. 9, or locator members with post-delivery actuation capabilities, such as those described above.

Bio-resorbable structures may be used in a number of configurations with the anchor members to accomplish the objectives of the various embodiments. The figures and the following description of exemplary embodiments address two structure embodiments, displacement structure and reinforcing structure. But any configuration or use of bio-resorbable structure to enable post-delivery actuation of filter anchor members can be utilized as part of the various embodiments.

Figure 9:
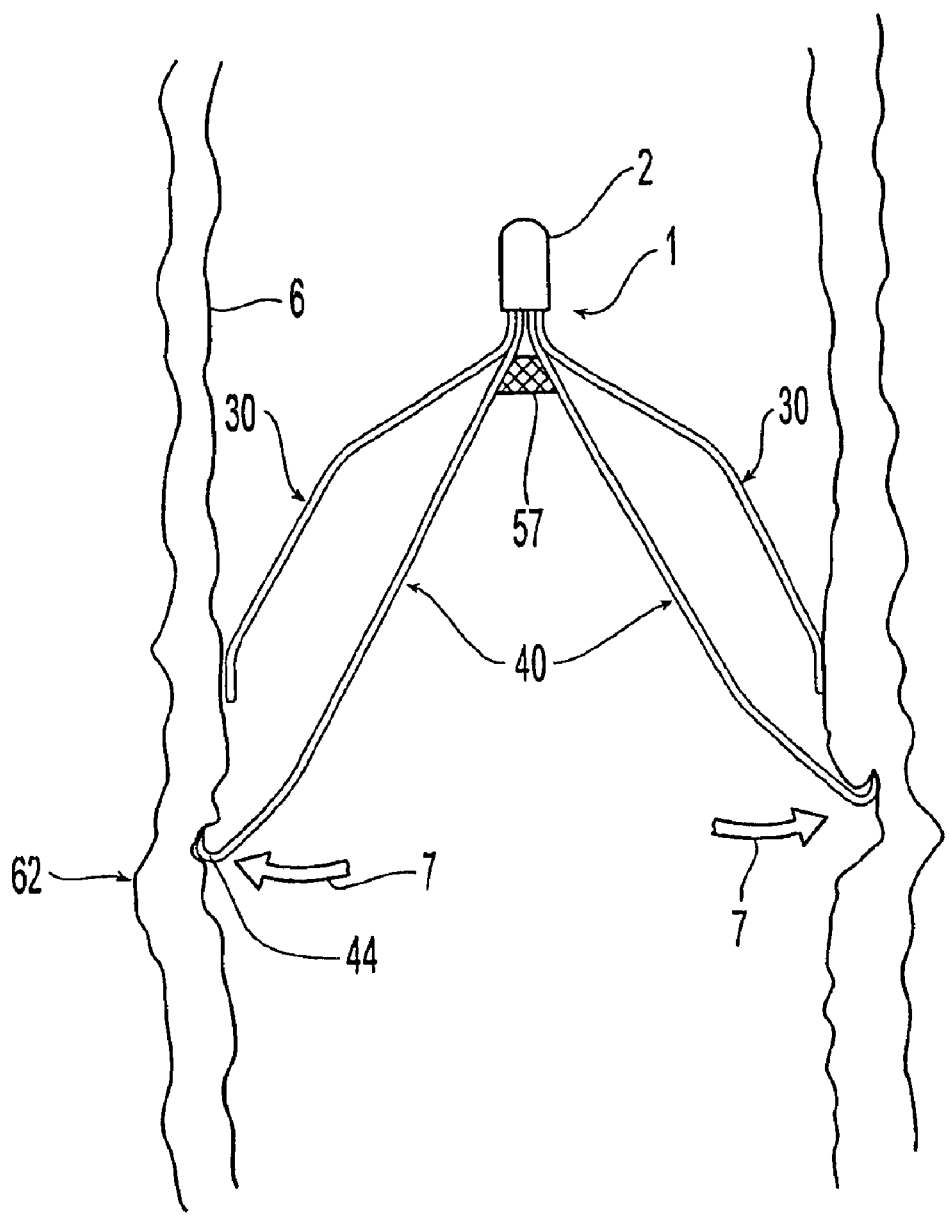
FIG. 9 is a plan view of the filter of FIG. 7A installed in a blood vessel.
Figure 10:
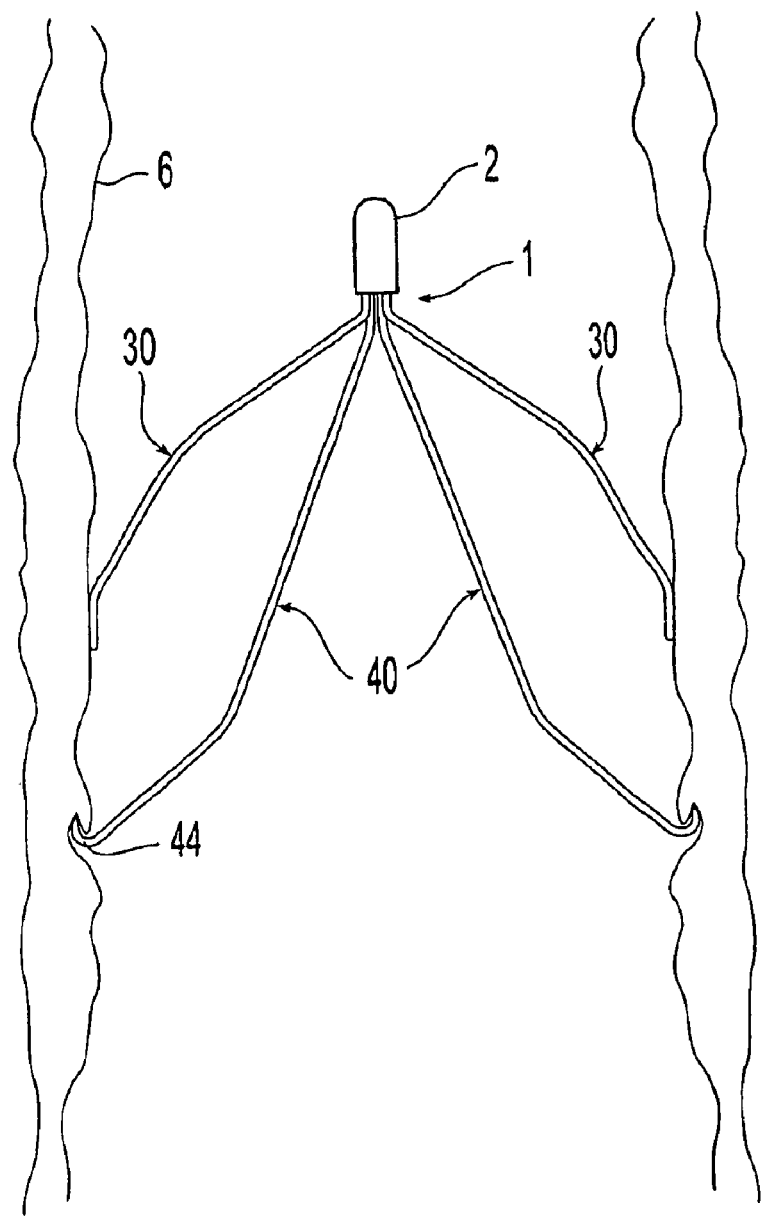
FIG. 10 is a plan view of the filter of FIG. 7B installed in a blood vessel after the bio-resorbable displacement wedge has bio-absorbed

A displacement structure embodiment for anchor members is illustrated in FIGS. 9-11C. Referring to FIG. 9, anchor members 40 may be initially displaced at their ends proximal the hub 2 by a bio-resorbable displacement structure 57 resulting in a first configuration. By pressing the anchor members 40 apart near their hub-ends, the displacement structure 57 causes the anchor members 40 to press against the blood vessel wall 6 with a force 7 which is sufficient to press the hooks 44 into the wall. This force 7 may also cause the walls to distend 62 somewhat. After delivery into the blood vessel, the displacement structure 57 begins to degrade (via hydrolytic or enzymatic degradation), eventually losing its strength and bio-absorbing away, which allows the anchor members 40 to return to their undisplaced second configuration illustrated in FIG. 10. In this second configuration, the hooks remain embedded in the vessel wall 6, but the force against the wall is relaxed so that there is little or no distention.

Figure 11A:
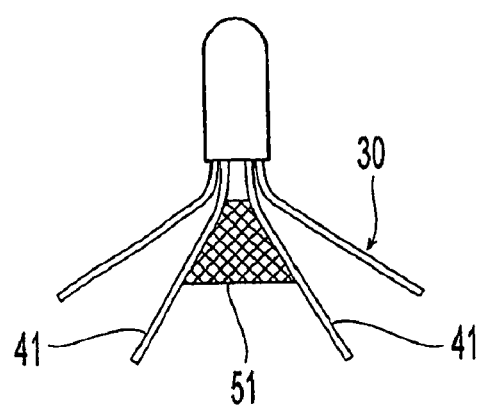
FIG. 11A is a detailed view of an alternative embodiment of the bio-resorbable displacement wedge of the filter of FIG. 9.
Figure 11B:
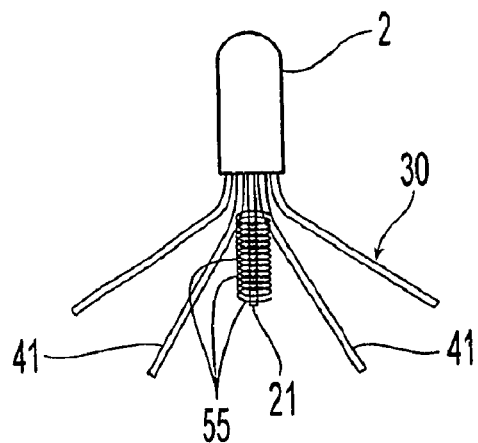
FIG. 11B is a detailed view of another alternative embodiment of the filter of FIG. 9 featuring the bio-resorbable displacement wraps of the filter of FIG. 8A.
Figure 11C:
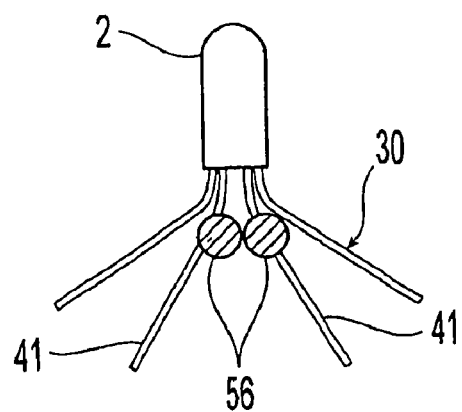
FIG. 11C is detailed view of another alternative embodiment of the filter of FIG. 9 featuring bio-resorbable displacement beads.

A number of embodiments of the displacement structure 57 can be utilized, including, by way of example but not by way of limitation, the three embodiments illustrated in FIGS. 11A-11C. Referring to FIG. 11A, the displacement structure may be in the form of a cone 51, plug, wedge, or similar form that is pressed between the first portion 41 of the anchor members 40. Referring to FIG. 11B, the displacement structure may be in the form of windings of bio-resorbable material, such as bio-resorbable suture 55, wrapped around a central structure, such as a center wire 21. Referring to FIG. 11C, the displacement structure may be in the form of beads 56 formed on each anchor member's first portion 41 so that when assembled on the hub 2, the beads contact one another, thereby forcing the anchor members 40 apart. Each of these embodiments of the displacement structure function by displacing the anchor members radially outward into a first configuration when the material is present, and allowing the anchor members 40 to return to their undisplaced second configuration upon bio-absorption.

Alternatively, a number of embodiments can include a bio-absorbing reinforcing structure can be utilized, two examples of which are illustrated in FIGS. 12A-13B. In this embodiment, the anchor members 40 may feature a narrow cross section portion 45, such as connected between the hub 2 and the rest of the first portion of anchor member 41. The narrow cross section portion 45 will have less strength, and thus will bend more easily under stress than the rest of the anchor member 41. Prior to delivery, the narrow cross section portion 45 is reinforced by a bio-resorbable structure so that the anchor members 40 as a group flex radially outward in a first configuration applying a force against the vessel wall 6 in order to drive the hooks 44 into the wall tissue. Then, after delivery, the bio-resorbable structure degrades and eventually is resorbed, leaving the narrow cross section portions 45 free to bend in response to the applied force into a second configuration (shown, for example, in FIG. 12B), thereby reducing the force applied to the vessel wall.

Figure 12A:
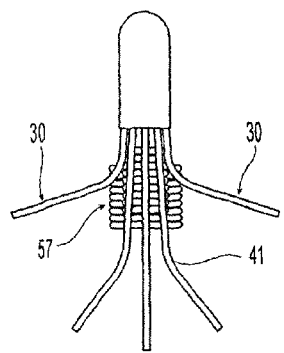
FIG. 12A is a detailed view of an alternative embodiment of the filter of FIG. 9 featuring a bio-resorbable wraps.
Figure 12B:
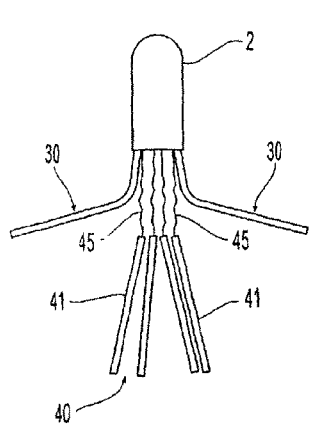
FIG. 12B is a detailed view of an alternative embodiment of the filter of FIG. 12A after the bio-resorbable wraps have bio-absorbed.

Referring to FIG. 12A, one approach for reinforcing the narrow cross section portion 45 is to wrap the upper portion of the anchor members 40 with bio-resorbable suture 57 (or similar bio-resorbable material). During assembly, the narrow cross section portion 45 and a portion of the anchor member first portions 41 may be wrapped with many layers of bio-resorbable sutures, holding these portions rigidly together so the anchor members 40 as a group flex radially outward into a first configuration applying a force against the vessel wall 6 in order to drive the hooks 44 into the wall tissue. Then, after a few weeks in the body, the sutures 57 will resorb, allowing the narrow cross section portion 45 to flex into a second configuration as illustrated in FIG. 12B.

Figure 13A:
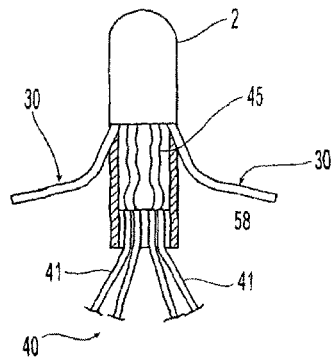
FIG. 13A is a detailed view of another alternative embodiment of the filter of FIG. 12A with a bio-resorbable sleeve.
Figure 13B:
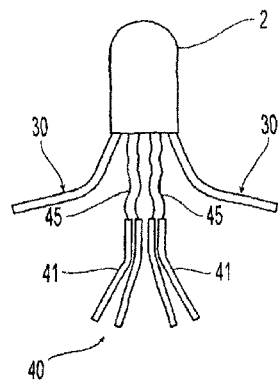
FIG. 13B is a detailed view of an alternative embodiment of the filter of FIG. 13A after the bio-resorbable sleeve has bio-absorbed.

Referring to FIG. 13A, another approach for reinforcing the narrow cross section portion 45 is to enclose them within a bio-resorbable sleeve 58. Similar to the above embodiment, the bio-resorbable sleeve reinforces the narrow cross section portion 45 and holds the anchor member first portions 41 rigidly together in a first configuration so the anchor members 40 as a group flex radially outward applying a force against the vessel wall 6 in order to drive the hooks 44 into the wall tissue. Then, after a few weeks in the body, the sleeve 58 will resorb, allowing the narrow cross section portion 45 to flex into a second configuration as illustrated in FIG. 13B.

In the embodiment illustrated in FIGS. 9-14B, the filter 1 may employ any of a number of alternative shapes of locator members. For example, such a filter may employ locator members similar to those described in U.S. Pat. No. 6,258,026, or in PCT International Application No. PCT/US06/017889, entitled "Removable Embolus Blood Clot Filter," which are hereby incorporated by reference in their entirety. An example of suitable shapes and dimensions of locator members for this embodiment are provided in FIG. 7B and table 2 herein.

In the various embodiments, bio-resorbable material, whether as a restraint, displacement and/or reinforcing structure, serves as an element for providing various means for delaying or timing the actuation of the filter members from a first configuration to a second configuration. This delayed actuation function may be accomplished using bio-resorbable material in any of the forms and configurations described herein, and their equivalents, in combination with the filter member configurations described herein. Further, the bio-resorbable material may be configured, formulated or compounded to provide actuation at a predicted or predetermined time after delivery into a subject and to enable actuation in a single movement, a sequence of small movements or in an extended, slow movement.

Figure 14A:
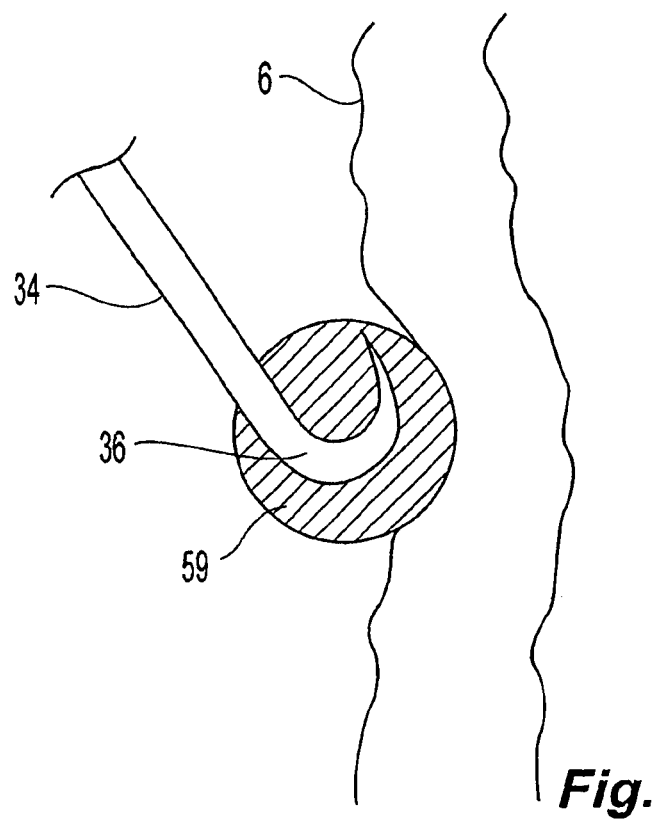
FIG. 14A is a detailed view of a hook portion of a locator or anchor member with a bio-resorbable cover.
Figure 14B:
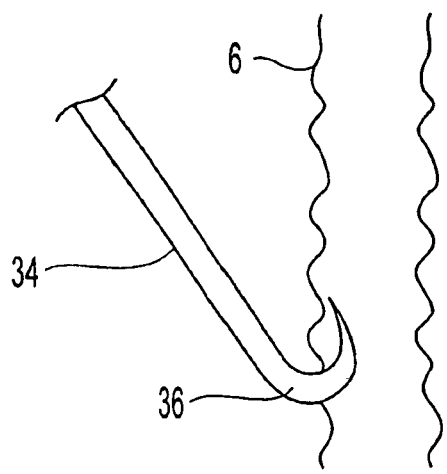
FIG. 14B is a detailed view of the hook portion shown in FIG. 14A after the bio-resorbable cover has bio-absorbed.

In another embodiment illustrated in FIGS. 14A and 14B, locator members 30 may be tipped with a hook 36 so that the locator members 30 can contribute to holding the filter in place within the blood vessel. In order to permit the locator members 30 to move easily over the walls of the blood vessel 6 during post-delivery actuation, the hook 36 needs to be covered until after the actuation motions are completed. As illustrated in FIG. 14A, the hook may be covered with a sufficient mass of bio-resorbable cover material 59 to encapsulate the tip of the hook 36 and present a smooth surface for sliding along the inside of the vessel 6. The bio-resorbable material 59 may be the same or different material as used in the bio-resorbable restraint or displacement structure. If the cover material 59 is the same as used for the locator 30 and/or anchor member 40 delayed actuation means, then a coating or additional mass may be employed to ensure the hook is uncovered after actuation motions are completed. Alternatively, a different, slower resorbing material may be used for the cover material 59 than used for the locator and/or anchor member delayed actuation means in order to ensure the hook is uncovered after actuation motions are completed.

In a further refinement of the aforementioned embodiments, the bio-resorbable material used to retain or displace filter members (either locators or anchors or both) may be configured or of a type that can be activated by an affirmative action of the clinician after implantation. This embodiment provides the clinician with more control over the period of time after delivery at which the filter changes shape. In a particular example embodiment, the material may be activated by exposure to radiation, preferably infrared (IR), visible or ultraviolet (UV) light, so that after irradiation the material becomes resorbable. This capability may be provided by adding radiation-excited, bio-compatible chemicals (such as dyes) to the resorbable material or coating the resorbable material with a radiation-sensitive water repellant coating. A suitable material or coating is one that changes chemical structure upon exposure to a particular activating wavelength of radiation (e.g., IR, UV or visible light). For example, a bio-resorbable restraint of any of the foregoing embodiments may be treated with a radiation-activated, water repellant coating. Such a coating prevents body fluids from degrading the resorbable material when the filter is first delivered into the blood vessel. For example, a waterproof coating may be sensitive to ultraviolet light so the coating changes chemical form, breaks polymer chains, or becomes porous when it absorbs UV energy. Prior to exposure to UV light, the coating prevents moisture or enzymes in the blood from degrading the bio-resorbable material. Once exposed, the coating resorbs or becomes porous so that hydrolytic or enzymatic degradation of the underlying bio-resorbable material can begin. Once exposed to the activating wavelength of radiation, the water repellant coating dissolves or becomes porous so that hydrolytic or enzymatic degradation of the underlying resorbable restraint can begin. In another example, exposure to a specific wavelength of light causes the light-activated coating to change structure which causes separation between the coating and the resorbable restraint, thereby allowing blood to reach the restraint. Since the radiation-activated material in this example is merely a coating and the bio-resorbable material carries the structural load inherent in the restraint, the amount of radiation required to initiate the degradation process may be quite modest.

In a particular example embodiment, the coating material applied to the bio-resorbable restraint may be polyethylene formulated with a melting point of about 60 degrees Celsius mixed with a biocompatible dye that absorbs radiation in the range approximately 800 nanometers (nm). Mammalian tissues tend to be substantially transparent to radiation around 800 nm, so the radiation may be applied through blood or even from the outside of a patient's body, such as by means of a laser. Indocyanine green is an example of a dye which absorbs radiation around 800 nm and is biocompatible. Such a biocompatible dye will preferentially absorb the light energy shown upon it, thereby raising the temperature in the polymer. When the polymer approaches or exceeds its approximate melting point temperature, about 60 degrees Celsius in this example, the polymer structurally weakens thereby causing the coating to lose integrity, leading to cracking or pealing to uncover at least a portion of the surface of the bio-resorbable restraint.

In another example, exposure to UV light may cause the material to lose its structural strength, resulting in the restraint promptly failing and immediate final positioning of the filter locator and/or anchor member.

Figure 15:
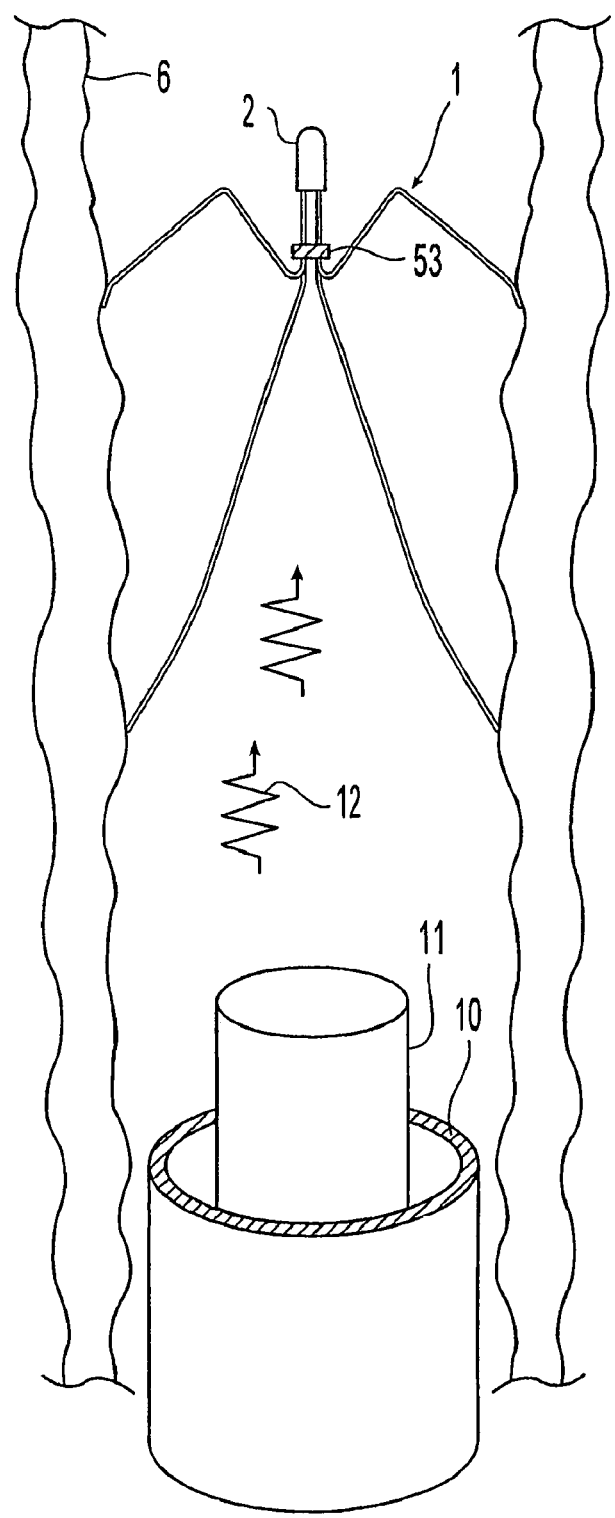
FIG. 15 shows a filter according to an embodiment being irradiated with light after implantation in a blood vessel.

Referring to FIG. 15, a filter 1 with post-delivery actuation capability according to one of the various embodiments described herein employs a bio-resorbable restraint 53 (and/or bio-resorbable displacement structure) where the restraint 53 is activated or stimulated by light, e.g., laser radiation 12. As illustrated in FIG. 15, a clinician may activate such a filter by shining radiation through a fiber optic imager 11 (fiber scope) positioned in the vicinity of the filter 1 via the same catheter 10 that delivered the filter to the blood vessel 6. In this embodiment, the clinician first delivers the filter 1 into a blood vessel, then before removing the catheter 10, the clinician may pass a fiber optic imager 11 through the catheter 10 and thereby conduct a visual inspection of the as-delivered filter 1. In order to displace blood to be able to view the filter, saline solution may be provided via the catheter 10. It the filter 1 is located, the clinician may then shine light 12, such as laser light (e.g., with a wavelength of about 800 nm), through the same fiber optic imager 11 to activate the filter, perhaps with saline solution flowing through the catheter 10 to displace blood. Alternatively, where laser light (e.g., with a wavelength of about 800 nm) is used, the light may be shined on the outside of the patient's body in close proximity to the filter to activate the bio-resorbable restraint through the skin.

This clinician-initiated deployment embodiment may further be used to control a first actuation that would cause the filter to deploy from a first configuration into a second configuration where retraction would be difficult, such as radial deployment of the locator 30 and anchor members 40, after inspecting the position and orientation of the filter. This embodiment would permit the clinician to inspect the delivered filter, such as by a fiber optic imager 11, and if improper actuation or deployment is indicated, reacquire and withdraw the filter via the delivery catheter 10. To permit this controlled deployment with retraction capability, a radiation actuated bio-resorbable material would be used to limit the expansion of the locators and/or anchors, such as by binding the members at their tips in a manner similar to those illustrated in FIGS. 5A-5C. Once proper positioning is verified, the radiation actuated bio-resorbable material binding the members may be irradiated via the fiber optic imager 11 or from outside the body through the skin via a laser, causing the material to lose strength and release the members. This embodiment may be used in combination with the other embodiments described herein to provide a three-configuration filter. In such a filter, a first configuration is the shape the filter assumes delivered but before activation by the clinician. When activated by the clinician, the first set of restraints is released so the filter assumes the second configuration where the members apply pressure to the vessel walls. Eventually, when the second bio-resorbable restraint or displacement materials are bio-absorbed away, the filter members assume the third configuration which eases the pressure applied to the vessel walls.

In a further embodiment, a method of implanting a filter in a blood vessel can be achieved. In this method, a clinician delivers a filter with post-delivery actuation capability, such as is described here, to a desired location in the blood vessel via a catheter. The filter may be pushed out of the catheter by a push wire. Once-positioned in a blood vessel the filter assumes a first configuration and the bio-resorbable structure is exposed to blood. After a period of time, exposure to blood leads to enzymatic or hydrolytic degradation of the bio-resorbable structure. Due to this degradation, the bio-resorbable structure breaks, compresses and/or is resorbed, allowing the filter members to assume a second configuration. In an additional step in the method, a clinician may activate the bio-resorbable structure after delivery to the blood vessel by exposing the structure to radiation, such as ultraviolet radiation delivered via a fiber optic imager.

In the foregoing embodiments, the material used for manufacturing the filter members (locators and anchors) may be any suitable bio-compatible flexible material such as, for example, polymer, memory polymer, memory metal, thermal memory material, metal, metal alloy, ceramics, or compressible spring metal such as stainless steel or a suitable plastic. Preferably, the material may be Elgiloy®, and most preferably Nitinol which is a thermal shape memory alloy, which can be super-elastic or linear-elastic in behavior.

The use of a thermal shape memory material, such as Nitinol, for the locator and anchor members facilitates collapsing the filter radially inward from its normally expanded configuration toward its longitudinal axis into a collapsed configuration for insertion into a body vessel via a catheter. Example methods for setting the high-temperature shape of filters are disclosed in U.S. Pat. No. 4,425,908, which is hereby incorporated by reference in its entirety.

By forming the locator and anchor members of a blood clot filter of a super-elastic material or Nitinol alloy material, such as Nitinol wire, transition between the martensitic and austenitic forms of the material can be achieved by temperature transitions above and below a transition temperature (referred to as the martensitic-to-austenitic transition temperature). Preferably, this transition temperature is at or below the subject's body temperature. Such controlled temperature transitions may be employed to soften and contract the Nitinol filter body to facilitate insertion into a storage tube or catheter and to subsequently expand and rigidify within a vascular or other passageway when the filter reaches body temperature.

By virtue of the characteristics of thermal shape memory material, the locator and anchor members can be cooled below the martensitic-to-austenitic transition temperature and then straightened and held in a collapsed, straight form that can pass through a catheter with an internal diameter of approximately two millimeters (2 mm), e.g., a No. 7 French internal diameter catheter. In its high temperature form, the filter recovers to a preformed filtering shape as illustrated in the Figures.

Filters according to the various embodiments may be delivered through a catheter or delivery tube to a generally centered position within a body vessel. Suitable delivery systems and methods are described, for example, in U.S. Pat. No. 6,258,026, as well as in PCT International Application No. PCT/US06/17890, entitled "Embolus Blood Clot Filter and Delivery System," which are hereby incorporated by reference in their entirety.

Several aspects of the various embodiments provide advantages over the known filters. In particular, the capability of causing filter elements to relax after proper implantation helps protect blood vessels from injury due to long term exposure to radial stress. Additionally, post-delivery actuation enables filter designs which are less susceptible to being dislodged.

Additionally, where implantation of a filter is intended to be only temporary (as in a vehicle trauma victim or in a gastric bypass operation), the filters described in the various embodiments herein can be recovered using the recovery device shown and described in U.S. Pat. No. 6,156,055, which is hereby incorporated by reference in its entirety.

Although the bio-resorbable materials described here are not active within the body, other bio-active agents can be incorporated with or within the bio-resorbable restraint material in the various embodiments. Such bio-active agents include (but are not limited to) pharmaceutic agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligonucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

While the present invention has been disclosed with reference to certain preferred embodiments, numerous modifications, alterations, and changes to the described embodiments are possible without departing from the sphere and scope of the present invention. Accordingly, it is intended that the present invention not be limited to the described embodiments, but that it have the full scope defined by the language of the following claims, and equivalents thereof.

What is claimed is:

1. A filter to be placed in a flow of blood through a blood vessel having a vessel wall, the filter comprising:
   a) a hub, the hub having first and second end portions and a longitudinal axis;
   b) a plurality of leg members extending generally in one direction, distally from the hub, each leg member having one end portion connected to said hub and another end portion that is a free end portion spaced away from said hub, wherein only some of said leg members are a first plurality of leg members that are positioned by a resorbable restraint coupled to spring portions of the first plurality of leg members so as to retain the first plurality of the leg members in a first configuration that provides a first spring force that is applied toward the vessel wall in a radially outward direction that is transverse to the longitudinal axis and at a said free end portion of the first plurality of the leg members and wherein at least a portion of the first plurality of leg members forms a first acute angle with the said longitudinal axis;
   c) a second plurality of leg members that are not retained by a resorbable restraint, wherein a portion of each leg of said second plurality of leg members connects to the hub; and
   d) wherein when the resorbable restraint has resorbed the first plurality of leg members that were positioned by the resorbable restraint assume a second configuration that rotates said spring portions to form a second acute angle relative to said longitudinal axis that is different from said first acute angle, wherein said second configuration provides a second spring force that is applied toward the vessel wall in a radially outward direction that is transverse to the longitudinal axis and at a free end of the second plurality of leg members, wherein the second spring force is lower than the first spring force so that vessel damage or injury due to continued application of said first spring force is reduced or eliminated.

2. The filter of claim 1, wherein the first plurality of leg members are locator members, each of the locator members including a tip and an elongated portion contiguous with the spring portions such that (I) in the first configuration the locator members apply a radial force against walls of the blood vessel when the filter is positioned in the blood vessel, and (ii) in the second configuration the locator members lie approximately contiguous to and apply a nominal pressure against the wall of the blood vessel when the filter is positioned in the blood vessel.

3. The filter according to claim 2, wherein each of the spring portions comprise a curved portion having a first end and a second end, the first end being coupled to the hub and the second end being coupled to the elongated portion, wherein further the resorbable restraint encircles the curved portions near their second ends.

4. The filter according to claim 3, wherein the elongated portions of the locator members comprise a first portion linearly coupled to the curved portion, and a second portion coupled to the tip portion, each of the first and second portions being generally linear and disposed on distinct axes each oblique to the longitudinal axis.

5. The filter according to claim 4, wherein the axes of the first and second portions form angle of approximately 90 degrees.

6. The filter according to claim 1, wherein the resorbable restraint comprises a resorbable material which is resorbed in blood.

7. The filter according to claim 6, wherein the resorbable material becomes soluble in blood after exposure to radiation.

8. The filter according to claim 1, wherein the bio-resorbable restraint comprises a sleeve of a resorbable material which is resorbed in blood.

9. The filter according to claim 1, wherein the resorbable restraint comprises a cone positioned between the spring portions so as to apply a radial force on the spring portions.

10. A filter to be placed in a blood vessel, the filter comprising:
    a) a hub disposed along a hub longitudinal axis;
    b) a plurality of anchor members coupled to the hub and extending generally in one direction distally of the hub, each anchor member including a hook that is spaced away from the hub and configured so that the hook penetrates a wall of the blood vessel when the filter is disposed in the blood vessel;
    c) a plurality of locator members, each locator member including:
       I) a first portion proximate the hub, the first portion including a spring portion;
       ii) a second portion that extends from the first portion along a first axis;
       iii) a third portion that extends from the second portion along a second axis, wherein the second axis is distinct from the first axis; and
       iv) a tip portion that is a free end portion and that extends from the third portion along a tip axis, wherein the tip axis is distinct from the first and second axes;
    d) a resorbable restraint coupled to the spring portions of the locator members and not coupled to the anchor members so as to retain the locator members in a first configuration wherein each locator member forms a first acute angle with said longitudinal axis and provides a first spring force that is applied toward the vessel wall in a radially outward direction that is transverse to the longitudinal axis and at said free end portion of each locator member; and
    e) wherein when the resorbable restraint has resorbed each locator member assumes a second configuration that moves said spring portions to form a second acute angle different from said first acute angle relative to said hub longitudinal axis, wherein said second configuration provides a second spring force that is applied toward the vessel wall in a radially outward direction that is transverse to the longitudinal axis and at a free end portion of each locator member, wherein the second spring force is lower than the first spring force so that vessel damage or injury due to continued application of said first spring force is reduced or eliminated; and
    f) wherein in said second configuration:
       I) the first and second portions of each locator member form an acute angle; and
       ii) the second and third portions of each locator member form an obtuse angle between said second and third portions.

11. The filter according to claim 10, wherein each of the first portions comprise a curved portion having at a first end coupled to the hub and a second end coupled to the second portion, wherein further the resorbable restraint encircles the curved portion near the second end.

12. The filter according to claim 10, wherein the resorbable restraint comprises a loop of a resorbable material which is resorbed in blood.

13. The filter according to claim 12, wherein the resorbable material becomes soluble in blood after exposure to ultraviolet radiation.

14. The filter according to claim 10, wherein the resorbable restraint comprises a sleeve of a resorbable material which is resorbed in blood.

15. The filter according to claim 10, wherein the resorbable restraint comprises a plug positioned between respective spring portions so as to apply a radial force on the spring portions.

16. The filter according to claim 10, wherein the tip portion of each of the plurality of locator members further comprises a hook and a bio-resorbable material encompassing at least a portion of the hook.

17. A filter to be placed in a blood vessel, comprising:
  a) a head having a head longitudinal axis;
  b) a plurality of filter members extending generally in one direction, distally from the head, said members including a first plurality of filter members and a second plurality of filter members;
  c) a resorbable member attached to the first plurality of the filter members for enabling a delay of movement of the first plurality of filter members following delivery of the filter into the blood vessel, wherein there is no resorbable member attached to the second plurality of filter members;
  d) wherein each filter member has a first portion connected to the head, a second portion connected to the first portion and a third portion connected to the second portion;
  e) wherein each of the first plurality of filter members is movable from: 1) a first configuration when the resorbable member holds the filter members of the first plurality together and wherein the first portion of each filter member of said first plurality of filter members forms a first acute angle with said longitudinal axis to second configuration wherein the resorbable member does not hold the filter members of the first plurality together, wherein in the second configuration filter members apply a reduced radial pressure against a vessel wall as compared to the first configuration;
  f) wherein in said second configuration:
    I) the first portion of each filter member of the first plurality form a second acute angle that differs from said first acute angle; and
    ii) the second and third portions of each filter member of the first plurality form an obtuse angle between said second and third portions.

18. A filter to be placed in a flow of blood through a blood vessel having a vessel wall, the filter comprising:
  a) a hub having first and second end portions and a longitudinal axis;
  b) a plurality of leg members extending generally in one direction distally from the hub, each leg member having one end portion connected to said hub and another end portion that is a free end portion spaced away from said hub, wherein only some of said leg members defining a first plurality of leg members are positioned by a bioresorbable restraint coupled to spring portions of the said first plurality of leg members so as to retain the first plurality of the leg members in a first configuration that provides a first spring force that is applied toward the vessel wall in a radially outward direction that is transverse to the longitudinal axis and at a said free end portion of the first plurality of the leg members and wherein at least a portion of the first plurality of leg members forms a first acute angle with the said longitudinal axis;
  c) a second plurality of leg members that are not retained by the bioresorbable restraint, wherein a portion of each leg of said second plurality of leg members connects to the hub and each leg of said second plurality includes a portion that forms an acute angle with said longitudinal axis; and
  d) wherein when the bioresorbable restraint has resorbed the first plurality of leg members that were positioned by the resorbable restraint assume a second configuration that rotates said spring portions relative to said longitudinal axis, wherein said second configuration provides a second spring force that is applied toward the vessel wall in a radially outward direction that is transverse to the longitudinal axis and at a free end of said first plurality of leg members, wherein the second spring force is lower than the first spring force.

* * * * *